United States Patent
Zhang et al.

(10) Patent No.: US 12,378,253 B2
(45) Date of Patent: Aug. 5, 2025

(54) PYRROLOPYRIMIDINE COMPOUND AS BTK INHIBITOR AND USE THEREOF

(71) Applicant: ZHEJIANG LONGCHARM BIO-TECH PHARMA. CO., LTD., Hangzhou (CN)

(72) Inventors: Yang Zhang, Shanghai (CN); Wentao Wu, Shanghai (CN); Kaijun Geng, Shanghai (CN); Qiu Li, Shanghai (CN); Jian Li, Shanghai (CN); Shuhui Chen, Shanghai (CN)

(73) Assignee: ZHEJIANG LONGCHARM BIO-TECH PHARMA. CO., LTD., Hangzhou (CN)

( * ) Notice: Subject to any disclaimer, the term of this patent is extended or adjusted under 35 U.S.C. 154(b) by 382 days.

(21) Appl. No.: 17/776,873

(22) PCT Filed: Nov. 13, 2020

(86) PCT No.: PCT/CN2020/128597
§ 371 (c)(1),
(2) Date: May 13, 2022

(87) PCT Pub. No.: WO2021/093839
PCT Pub. Date: May 20, 2021

(65) Prior Publication Data
US 2023/0357248 A1    Nov. 9, 2023

(30) Foreign Application Priority Data

Nov. 13, 2019 (CN) .......................... 201911109773.2
Dec. 13, 2019 (CN) .......................... 201911288492.8
Feb. 17, 2020 (CN) .......................... 202010096582.3
Jul. 22, 2020 (CN) .......................... 202010711270.9

(51) Int. Cl.
  *C07D 487/04* (2006.01)
  *A61K 31/519* (2006.01)
  *A61P 35/00* (2006.01)

(52) U.S. Cl.
  CPC .......... *C07D 487/04* (2013.01); *A61K 31/519* (2013.01); *A61P 35/00* (2018.01)

(58) Field of Classification Search
  CPC ...... A61P 35/00; C07D 487/04; A61K 31/519
  See application file for complete search history.

(56) References Cited

U.S. PATENT DOCUMENTS 11,020,398 B2 *  6/2021  Bates .................... A61P 37/06
2018/0055846 A1  3/2018  Bates et al.

FOREIGN PATENT DOCUMENTS

CN    108699062 A    10/2018
CN    109890821 A    6/2019

OTHER PUBLICATIONS

Ciapetti et al., "Chapter 15—Molecular Variations Based on Isosteric Replacements", The Practice of Medicinal Chemistry (Third Edition), 2008, pp. 290-342.
Partial Supplementary European Search Report issued by the European Patent Office (European Application No. 20887944.5, mailed Oct. 26, 2023).

* cited by examiner

*Primary Examiner* — James H Alstrum-Acevedo
*Assistant Examiner* — Carolyn L. Ladd
(74) *Attorney, Agent, or Firm* — Mintz Levin Cohn Ferris Glovsky and Popeo, P.C.

(57) ABSTRACT

Disclosed are a pyrrolopyrimidine compound and a use thereof in preparing a medicine for diseases related to a BTK protein kinase inhibitor. Specially, disclosed are a compound as shown in formula (III) and a pharmaceutically acceptable salt thereof.

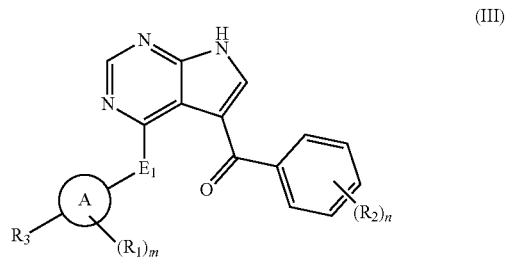

11 Claims, 3 Drawing Sheets

PYRROLOPYRIMIDINE COMPOUND AS BTK INHIBITOR AND USE THEREOF

The present application is a United States National Phase under 35 U.S.C. § 371 of International Application No. PCT/CN2020/128597, filed Nov. 13, 2020, which claims the priority of: CN201911109773.2, filed on Nov. 13, 2019; CN201911288492.8, filed on Dec. 13, 2019; CN202010096582.3, filed on Feb. 17, 2020; and CN202010711270.9, filed on Jul. 22, 2020.

FIELD OF THE INVENTION

The present disclosure relates to a pyrrolopyrimidine compound and use thereof in the manufacture of a medicament for treating diseases related to BTK protein kinase.

BACKGROUND OF THE INVENTION

The pyrrolopyrimidine compound of the present disclosure is a new class of protein kinase inhibitor, which has various therapeutic applications and can be used for the treatment of disorders related to proliferation, inflammation and autoimmunity caused by protein kinases.

Kinase is a class of enzyme that controls the transfer of phosphate group from phosphate donor (e.g. ATP) to specific substrate. Protein kinase is a large subset of kinase and plays a central role in regulating a variety of cellular signals and processes. BTK is one of protein kinases.

BTK is a member of TEC cytoplasmic tyrosine kinase family (TEC family kinases, TFKs). There are 5 members in this family. In addition to BTK, there are ITK, TEC, BMX and TXK. TFKs have an evolutionary history of more than 600 million years, belong to a very old kinase family, and mainly play a role in the hematopoietic system.

BTK is mainly responsible for the transduction and amplification of various intracellular and extracellular signals in B lymphocytes, and is necessary for B cell maturation. Inactivation of BTK function in XLA patients results in a deficiency of peripheral B cell and immunoglobulin. Signaling receptors upstream of BTK include growth factor and cytokine receptors, G protein-coupled receptors such as chemokine receptors, antigen receptors (especially B cell receptors [BCR]), and integrins, etc. BTK in turn activates many major downstream signaling pathways, including phosphoinositide-3 kinase (PI3K)-AKT pathway, phospholipase-C (PLC), protein kinase C, and nuclear factor κ B (NF-κB), etc. The role of BTK in BCR signaling and cell migration is well established, and these functions also appear to be major targets of BTK inhibitor. Increased BTK activity has been detected in blood cancer cells such as B-cell chronic lymphocytic leukemia (CLL) and mantle cell lymphoma (MCL), etc. Abnormal activity of BTK function frequently leads to B-cell malignancies or autoimmune diseases, making it a popular target for research and development.

Currently, BTK inhibitors approved by FDA for marketing include ibrutinib and acalabrutinib (acalanib). These two irreversible covalent inhibitors can form covalent binding with protein C481, thereby effectively inhibiting the activity of BTK. Clinical studies have found that patients can develop resistance mutations after administration of ibrutinib and acalabrutinib (acalanib), including C481S, C481Y, C481R, C481F. For drug resistance caused by protein cysteine C481 mutation, we have designed and synthesized a series of irreversible BTK inhibitors of pyrrolopyrimidines.

SUMMARY OF THE INVENTION

The present disclosure provides a compound represented by formula (III) or a pharmaceutically acceptable salt thereof,

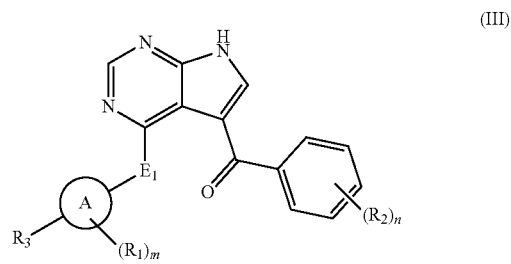

(III)

wherein, $R_1$ is selected from halogen and $C_{1-3}$ alkoxy, wherein the $C_{1-3}$ alkoxy is optionally substituted by 1, 2 or 3 $R_a$;

or, two $R_1$ can form cyclopropyl together with the bonds to which they are connected;

each $R_a$ is selected from D, halogen and OH;

$R_2$ is selected from halogen, methyl, phenoxy and pyridyloxy, wherein the phenoxy and pyridyloxy are optionally substituted with 1, 2 or 3 halogens;

$R_3$ is selected from —$CH_2OH$, and m is selected from 1 and 2;

or $R_3$ is selected from CN and $CH_2CN$, and m is selected from 0, 1 and 2;

n is selected from 1, 2 and 3;

$E_1$ is selected from O, S and NH;

ring A is tetrahydropyranyl.

In some embodiments disclosed herein, each of the above-mentioned $R_a$ is selected from D, F and OH, and other variables are as defined herein.

In some embodiments disclosed herein, the above-mentioned $R_1$ is selected from F, $OCH_3$, $OCD_3$ and $OCH_2CH_2OH$, and other variables are as defined herein.

In some embodiments disclosed herein, the above-mentioned $R_2$ is selected from F, Cl, methyl, phenoxy, 2-fluorophenoxy and 2-pyridyloxy, and other variables are as defined herein.

In some embodiments disclosed herein, the above-mentioned $E_1$ is NH, and other variables are as defined herein.

In some embodiments disclosed herein, the above-mentioned ring A is

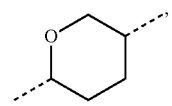

and other variables are as defined herein.

The present disclosure provides a compound represented by formula (I) or a pharmaceutically acceptable salt thereof,

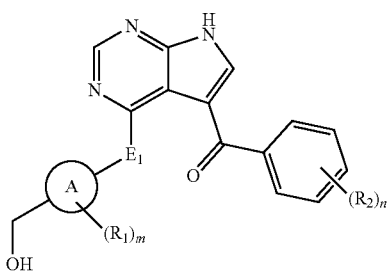

R₁ is selected from halogen;
or, two R₁ can form cyclopropyl together with the bonds to which they are connected;
R₂ is selected from halogen and phenoxy;
m and n are each independently selected from 1, 2 and 3;
E₁ is selected from O, S and NH;
ring A is tetrahydropyran ring.

In some embodiments disclosed herein, the above-mentioned R₁ is selected from F; or, two R₁ can form cyclopropyl together with the bonds to which they are connected, and other variables are as defined herein.

In some embodiments disclosed herein, the above-mentioned R₂ is selected from Cl and phenoxy, and other variables are as defined herein.

In some embodiments disclosed herein, the above-mentioned E₁ is NH, and other variables are as defined herein.

In some embodiments disclosed herein, the above-mentioned ring A is

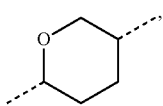

and other variables are as defined herein.

The present disclosure provides a compound represented by formula (III) or a pharmaceutically acceptable salt thereof,

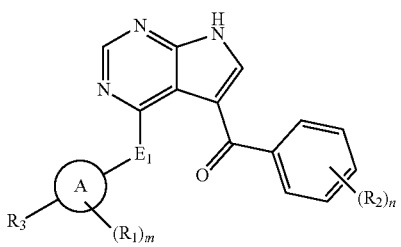

wherein,
R₁ is selected from halogen and $C_{1-3}$ alkoxy, wherein the $C_{1-3}$ alkoxy is optionally substituted by 1, 2 or 3 halogens;
or, two R₁ can form cyclopropyl together with the bonds to which they are connected;
R₂ is selected from halogen and phenoxy;
R₃ is selected from —CH₂OH, and m is selected from 1 and 2;
or R₃ is selected from CN and CH₂CN, and m is selected from 0, 1 and 2;

n is selected from 1, 2 and 3;
E₁ is selected from O, S and NH;
ring A is tetrahydropyranyl.

In some embodiments disclosed herein, the above-mentioned R₁ is selected from H, F and OCH₃, wherein the OCH₃ is optionally substituted by 1, 2 or 3 halogens, and other variables are as defined herein.

In some embodiments disclosed herein, the above-mentioned R₁ is selected from H, F and OCH₃, and other variables are as defined herein.

In some embodiments disclosed herein, the above-mentioned R₂ is selected from Cl and phenoxy, and other variables are as defined herein.

In some embodiments disclosed herein, the above-mentioned E₁ is NH, and other variables are as defined herein.

In some embodiments disclosed herein, the above-mentioned ring A is

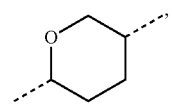

and other variables are as defined herein.

The present disclosure provides a compound represented by formula (III) or a pharmaceutically acceptable salt thereof,

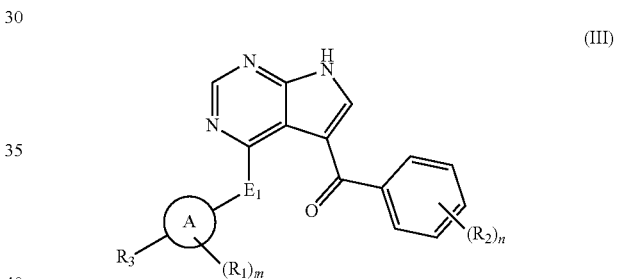

wherein,
R₁ is selected from halogen and $C_{1-3}$ alkoxy, wherein the $C_{1-3}$ alkoxy is optionally substituted by 1, 2 or 3 $R_a$;
or, two R₁ can form cyclopropyl together with the bonds to which they are connected;
each $R_a$ is selected from halogen and OH;
R₂ is selected from halogen, methyl, phenoxy and pyridyloxy, wherein the phenoxy and pyridyloxy are optionally substituted with 1, 2 or 3 halogens;
R₃ is selected from —CH₂OH, and m is selected from 1 and 2;
or R₃ is selected from CN and CH₂CN, and m is selected from 0, 1 and 2;
n is selected from 1, 2 and 3;
E₁ is selected from O, S and NH;
ring A is tetrahydropyranyl.

In some embodiments disclosed herein, each of the above-mentioned $R_a$ is selected from F and OH, and other variables are as defined herein.

In some embodiments disclosed herein, the above-mentioned R₁ is selected from F, OCH₃, OCD₃ and OCH₂CH₂OH, and other variables are as defined herein.

In some embodiments disclosed herein, the above-mentioned R₂ is selected from F, Cl, methyl, phenoxy, 2-fluorophenoxy and 2-pyridyloxy, and other variables are as defined herein.

In some embodiments disclosed herein, the above-mentioned $E_1$ is NH, and other variables are as defined herein.

In some embodiments disclosed herein, the above-mentioned ring A is

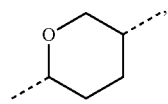

and other variables are as defined herein.

In some embodiments disclosed herein, the above-mentioned compound is selected from

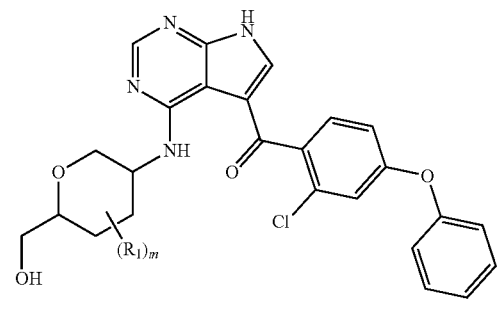
(I-1)

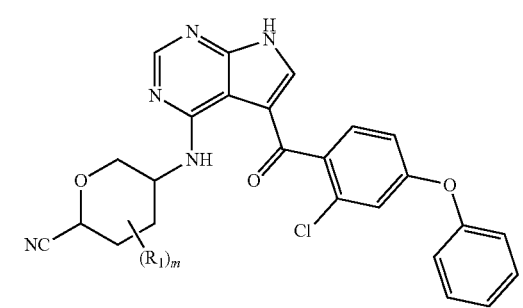
(III-1)

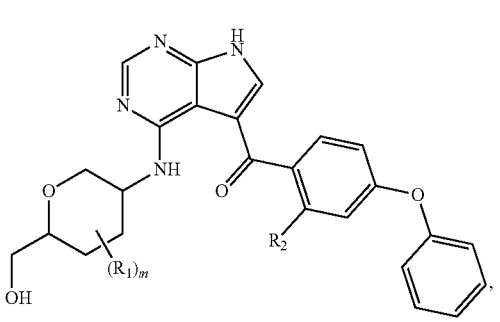
(IV-1)

wherein $R_1$, $R_2$ and m are as defined herein,
or a pharmaceutically acceptable salt thereof.

The present disclosure also includes some embodiments that are obtained by combining any of the above-mentioned variables.

The present disclosure also provides a compound selected from:

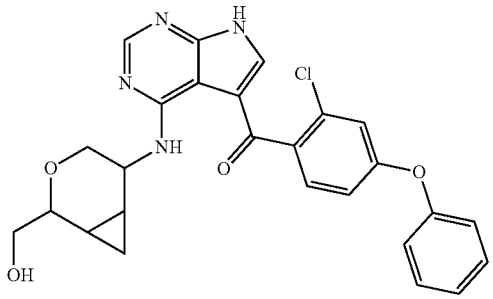

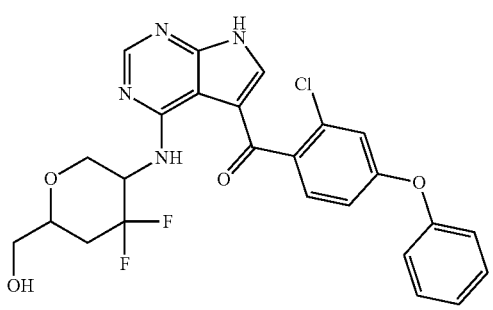

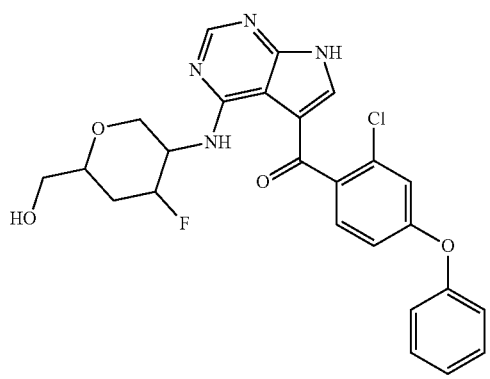

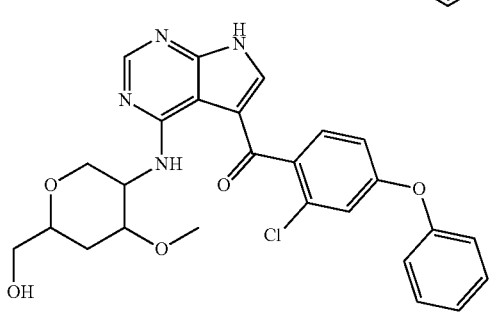

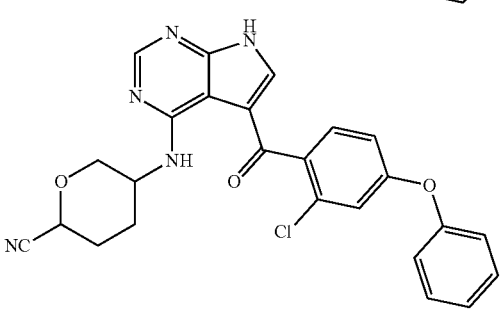

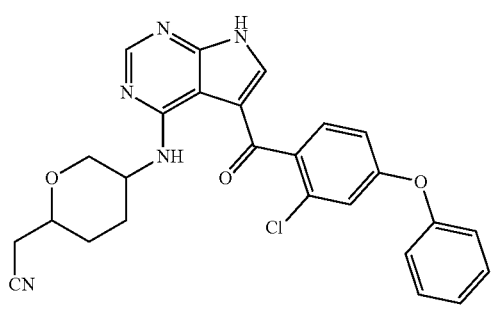
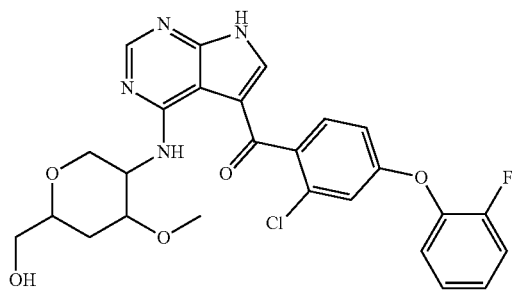
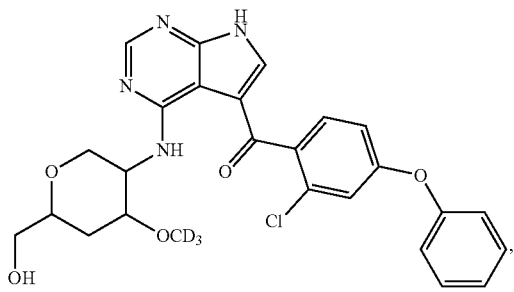
or a pharmaceutically acceptable salt thereof.
The present disclosure also provides a compound selected from:
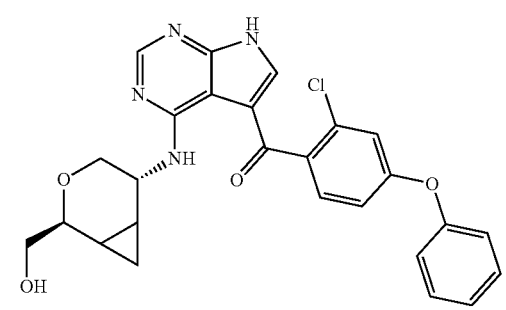
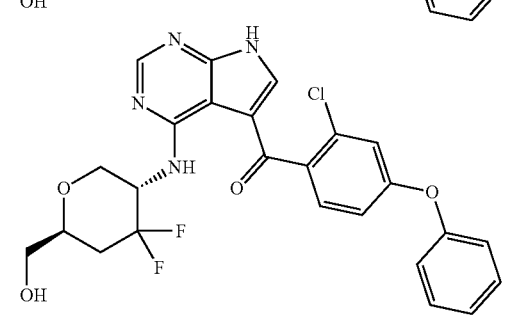
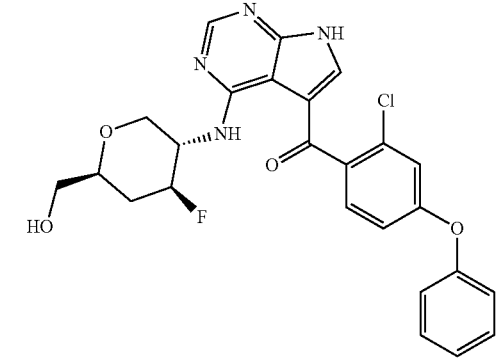

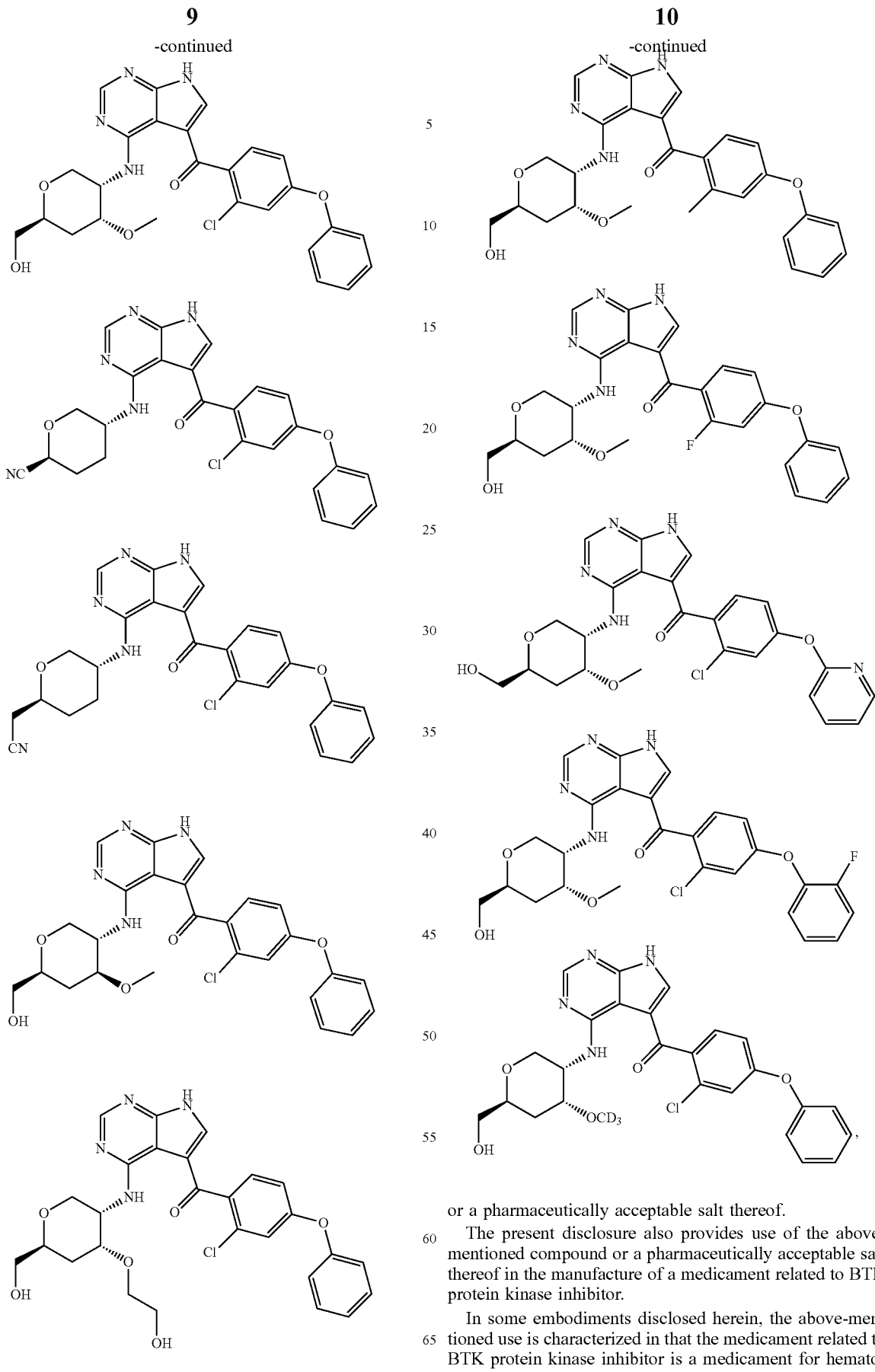

or a pharmaceutically acceptable salt thereof.

The present disclosure also provides use of the above-mentioned compound or a pharmaceutically acceptable salt thereof in the manufacture of a medicament related to BTK protein kinase inhibitor.

In some embodiments disclosed herein, the above-mentioned use is characterized in that the medicament related to BTK protein kinase inhibitor is a medicament for hematological neoplasm.

TECHNICAL EFFECT

The compound of the present disclosure has a strong inhibitory effect on $BTK^{C481S}$ mutation, and has a good inhibitory effect on TMD8 cells. The free drug concentration of compound 4 of the present disclosure in mouse and rat plasma is higher than that of reference example 1, and the inhibitory effect of compound 4 of the present disclosure on tumor is significantly better than that of reference example 1.

DEFINITION AND TERMS

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Unless otherwise specified, the term "isomer" is intended to include geometric isomers, cis- or trans-isomers, stereoisomers, enantiomers, optical isomers, diastereomers, and tautomers.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" means stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" means a stereoisomer in which two or more chiral centers of are contained in a molecule and is in a non-mirrored relationship between molecules.

Unless otherwise specified, "(+)" means dextroisomer, "(−)" means levoisomer, and "(±)" means racemate.

Unless otherwise specified, a wedged solid bond (⬧) and a wedged dashed bond (⬧) indicate the absolute configuration of a stereocenter; a straight solid bond (⬧) and a straight dashed bond (⬧) indicate the relative configuration of a stereocenter; a wavy line (⬧) indicates a wedged solid bond (⬧) or a wedged dashed bond (⬧); or a wavy line (⬧) indicates a straight solid bond (⬧) and a straight dashed bond (⬧).

Compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2, 4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to afford the pure enantiomer. In addition, the enantiomer and the diastereoisomer are generally isolated through chromatography which uses a chiral stationary phase and optionally combines with a chemical derivative method (for example, carbamate generated from amine).

Compounds disclosed herein may contain an unnatural proportion of atomic isotopes at one or more of the atoms that make up the compounds. For example, a compound may be labeled with a radioisotope such as tritium ($^3H$), iodine-125 ($^{125}I$) or C-14($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

Unless otherwise specified, the term "$C_{1-3}$ alkoxy" refers to an alkyl group containing 1 to 3 carbon atoms and attached to the remainder of a molecule by an oxygen atom. The $C_{1-3}$ alkoxy includes $C_{1-2}$, $C_{2-3}$, $C_3$ and $C_2$ alkoxy, and the like. Examples of $C_{1-3}$ alkoxy include, but are not limited to, methoxy, ethoxy, propoxy (including n-propoxy and isopropoxy), and the like.

Unless otherwise specified, the term "halo" or "halogen" by itself or as part of another substituent represents a fluorine, chlorine, bromine or iodine atom.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When an enumerated linking group does not indicate its linking direction, its linking direction is arbitrary. For example, when the linking group L in

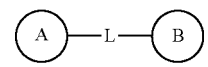

is -M-W—, the -M-W— can be linked to the ring A and the ring B in the same direction as the reading order from left to right to constitute

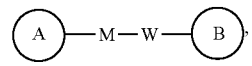

or can be linked to the ring A and the ring B in the reverse direction as the reading order from left to right to constitute

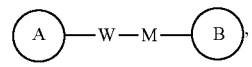

A combination of the linking groups, substituents and/or variants thereof is allowed only when such combination can result in a stable compound.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Solvents used in the present disclosure are commercially available. The following abbreviations are used in the present disclosure: aq represents aqueous; eq represents equivalent or equivalence; M represents mol/L; DCM represents dichloromethane; PE represents petroleum ether; DMF represents N,N-dimethylformamide; NMP represents N-methylpyrrolidone; DMSO represents dimethyl sulfoxide; EtOAc represents ethyl acetate; EtOH represents ethanol; MeOH represents methanol; CBz represents benzyloxycarbonyl, which is an amine protecting group; Boc represents tert-butoxycarbonyl, which is an amino protecting group; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; mp represents melting point.

Compounds are named according to general naming principles in the art or by ChemDraw® software, and commercially available compounds are named with their vendor directory names.

TECHNICAL EFFECT

The compound of the present disclosure has a strong inhibitory effect on BTK$^{C481S}$ mutation, and has a good inhibitory effect on TMD8 cells. The free drug concentration of compound 4 of the present disclosure in mouse and rat plasma is higher than that of reference example 1, and the inhibitory effect of compound 4 of the present disclosure on tumor was significantly better than that of reference example 1.

DETAILED DESCRIPTION OF THE INVENTION

Figure 1:
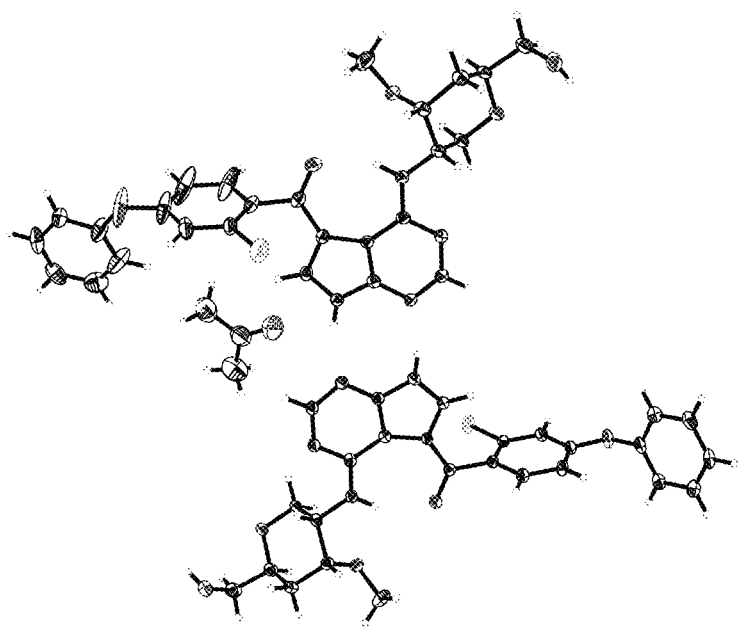
FIG. 1: ellipsoid diagram of the bimolecular stereostructure.
Figure 2:
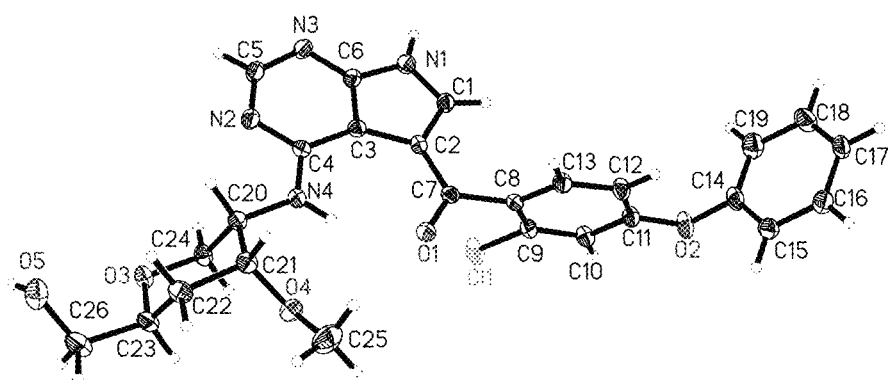
FIG. 2: ellipsoid diagram of the unimolecular stereostructure.
Figure 3:
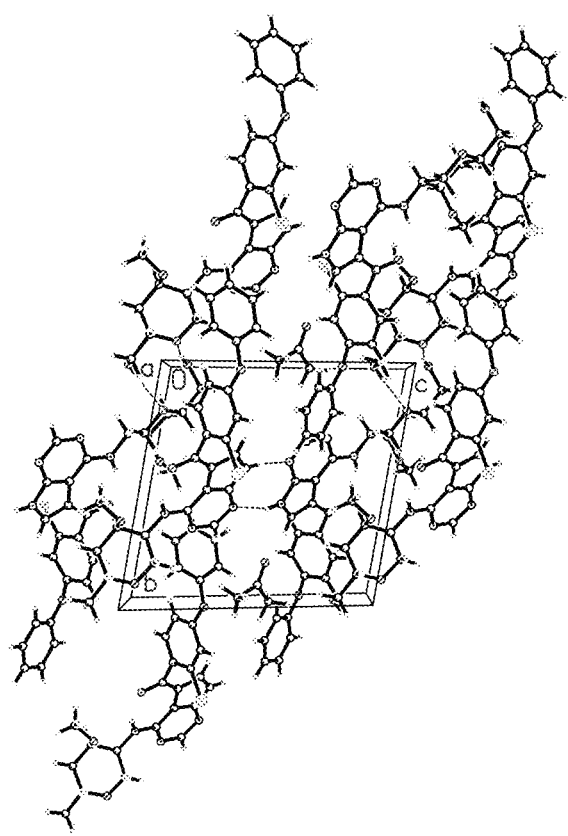
FIG. 3: unit cell stacking diagram along the a-axis direction.
Figure 4:
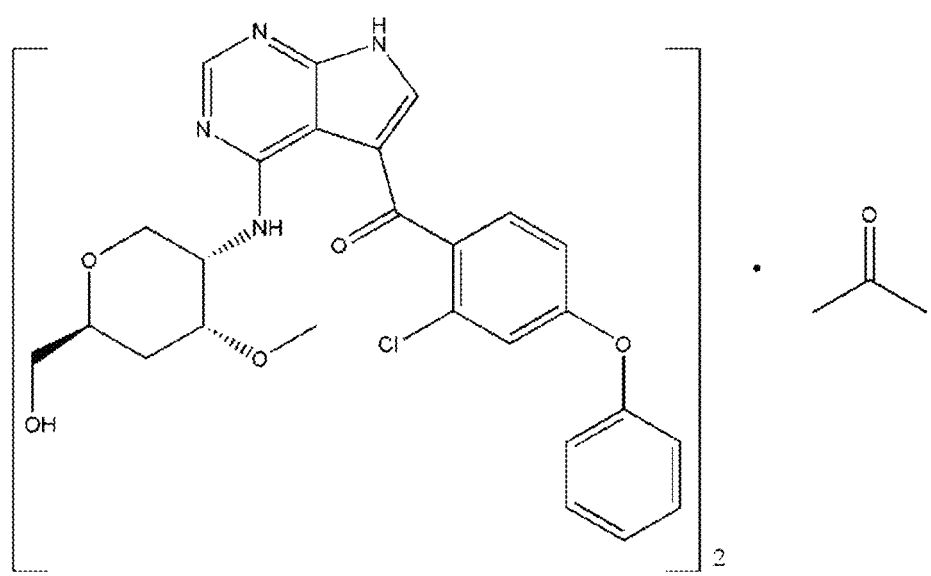
FIG. 4: absolute configuration diagram of the compound.

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Intermediate A

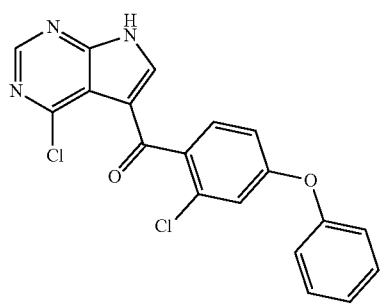 [SMILES: O=C(c1ccc(Oc2ccccc2)cc1Cl)c1c[nH]c2ncnc(Cl)c12]

Route for Synthesis:

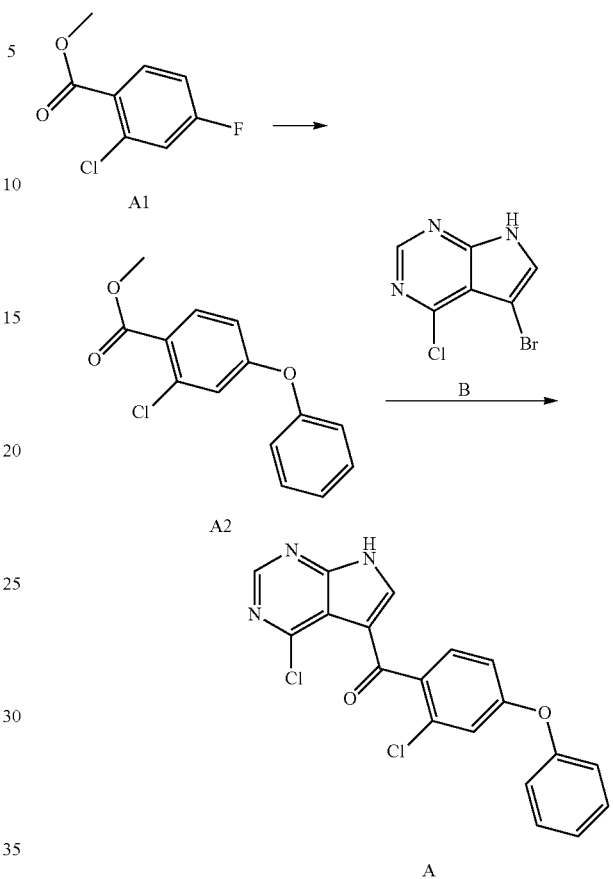

Step 1: Synthesis of Compound A2

Phenol (7.49 g, 79.54 mmol, 7.00 mL, 1.5 eq), compound A1 (10 g, 53.03 mmol, 1 eq), and cesium carbonate (25.92 g, 79.54 mmol, 1.5 eq) were dissolved in N,N-dimethylformamide (20 mL), and the mixture was reacted at 80° C. for 3 hours. After completion of the reaction, the reaction solution was filtered, and water was added. The mixture was extracted with ethyl acetate (100 mL×3). The organic phases were combined, dried over anhydrous sodium sulfate, and rotary evaporated to remove the solvent. The residue was purified by column chromatography (petroleum ether:ethyl acetate=10:1) to give compound A2. LCMS: (ESI) m/z: 263.1 [M+1].

Step 2: Synthesis of Compound A

Compound B (6 g, 25.81 mmol, 1 eq) was added to tetrahydrofuran (180 mL). The mixture was cooled to −78° C. (suspension, partially dissolved), and n-butyllithium (2.5 M, 21.68 mL, 2.1 eq) was then added dropwise. After completion of the addition, the mixture was reacted with stirring at −78° C. for 1 hour. A solution of compound A2 (7.12 g, 27.10 mmol, 1.05 eq) in tetrahydrofuran (10 mL) was then added dropwise, and the mixture was then stirred for another 1 hour. After completion of the reaction, the reaction was quenched with saturated ammonium chloride and stirred for 5 minutes. The organic phase was separated, and the aqueous phase was extracted with ethyl acetate (100 mL×3). The organic phases were combined and concentrated to give a crude intermediate A. LCMS: (ESI) m/z: 384.2 [M+1].

Example 1

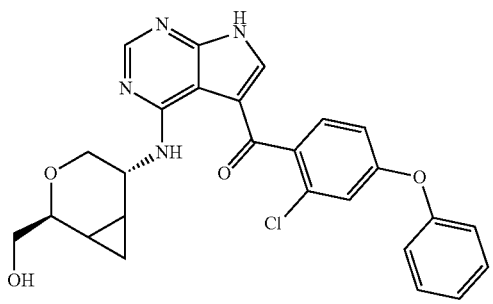

Route for Synthesis:

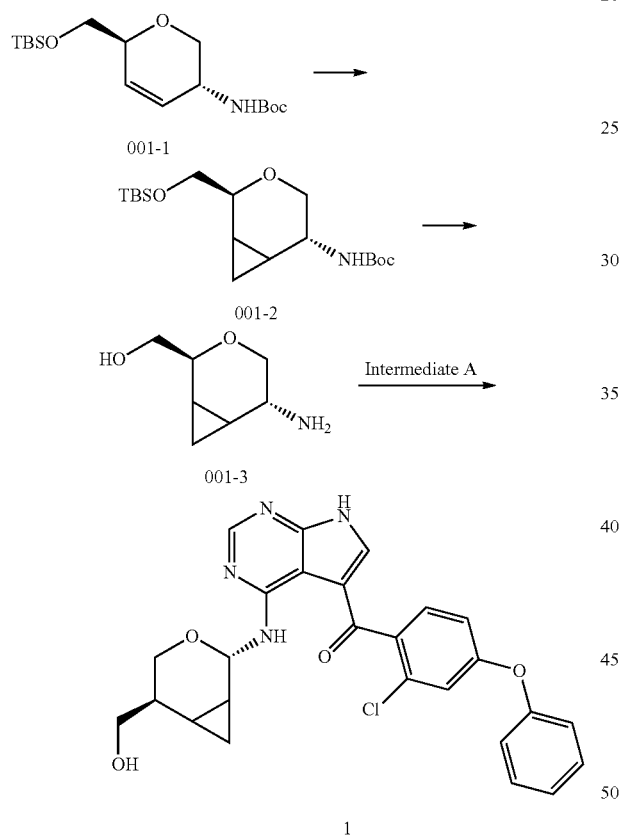

Compound 001-1 was obtained according to the synthesis procedures of compound 21 reported in Eur. J. Org. Chem. 2003, 2418-2427.

Step 1: Synthesis of Compound 001-2

Dichloroiodomethane (779.65 mg, 2.91 mmol, 234.83 μL, 2 eq) was dissolved in dichloromethane (10 mL), and diethylzinc (1 M, 2.91 mL, 2 eq) was added at 0° C. The mixture was stirred for 0.5 h, and then trifluoroacetic acid (331.91 mg, 2.91 mmol, 215.53 μL, 2 eq) was added. The mixture was then stirred for another 0.5 h. Compound 001-1 was added. After completion of the addition, the mixture was reacted at 20° C. for 1 h. After completion of the reaction, the reaction was quenched by adding saturated ammonium chloride to the reaction solution. The mixture was extracted with ethyl acetate (10 mL×3). The organic phases were washed with saturated brine, dried over anhydrous sodium sulfate and concentrated under vacuum to give compound 001-2. LCMS: (ESI) m/z: 380.2 [M+Na].

Step 2: Synthesis of Compound 001-3

Compound 001-2 (0.05 g, 139.84 μmol, 1 eq) was dissolved in 1,4-dioxane (1 mL), and hydrochloric acid/dioxane (4 M, 349.59 μL, 10 eq) was added. After completion of the addition, the mixture was reacted at 20° C. for 1 h. After completion of the reaction, the reaction solution was concentrated under reduced pressure to give compound 001-3, which was directly used in the next step without further purification. LCMS: (ESI) m/z: 144.2 [M+1].

Step 3: Synthesis of Compound 1

Compound 001-3 (20.02 mg, 139.84 μmol, 1 eq) was dissolved in isopropanol (5 mL), and intermediate A (53.73 mg, 139.84 μmol, 1 eq) and N,N-diisopropylethylamine (45.18 mg, 349.60 μmol, 60.89 μL, 2.5 eq) were added. After completion of the addition, the mixture was reacted with microwave at 130° C. for 2 h. After completion of the reaction, the mixture was concentrated under vacuum to give a crude product. The crude product was purified by preparative separation (chromatographic column: Welch Xtimate C18 150 mm*25 mm*5 μm; Mobile phase: [water (0.225% FA)-ACN]; B (acetonitrile) %: 35%-65%, 8 min) to give compound 1. LCMS: (ESI) m/z: 491.1 [M+1]. $^1$H NMR (400 MHz, CDCl$_3$) δ 8.87 (br d, J=7.78 Hz, 1H), 8.27 (s, 1H), 7.33-7.40 (m, 3H), 7.28 (s, 1H), 7.16 (s, 1H), 7.00-7.05 (m, 3H), 6.90 (dd, J=2.13, 8.41 Hz, 1H), 4.80-4.95 (m, 1H), 4.09 (dd, J=6.53, 11.54 Hz, 1H), 3.65-3.80 (m, 2H), 3.54-3.63 (m, 1H), 2.79 (t, J=10.92 Hz, 1H), 1.04-1.31 (m, 2H), 0.87-0.98 (m, 1H), 0.74-0.85 (m, 1H).

Example 2

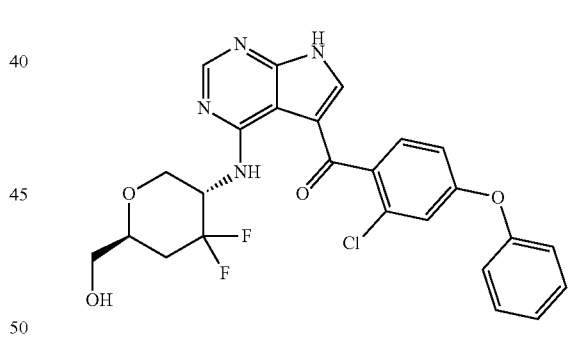

Route for Synthesis:

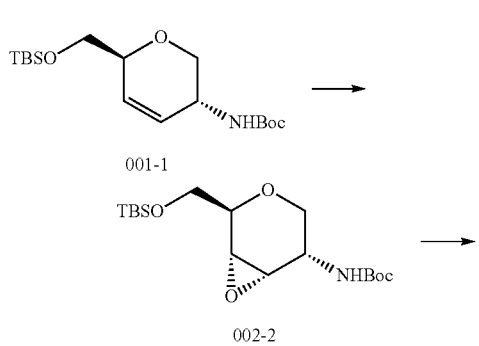

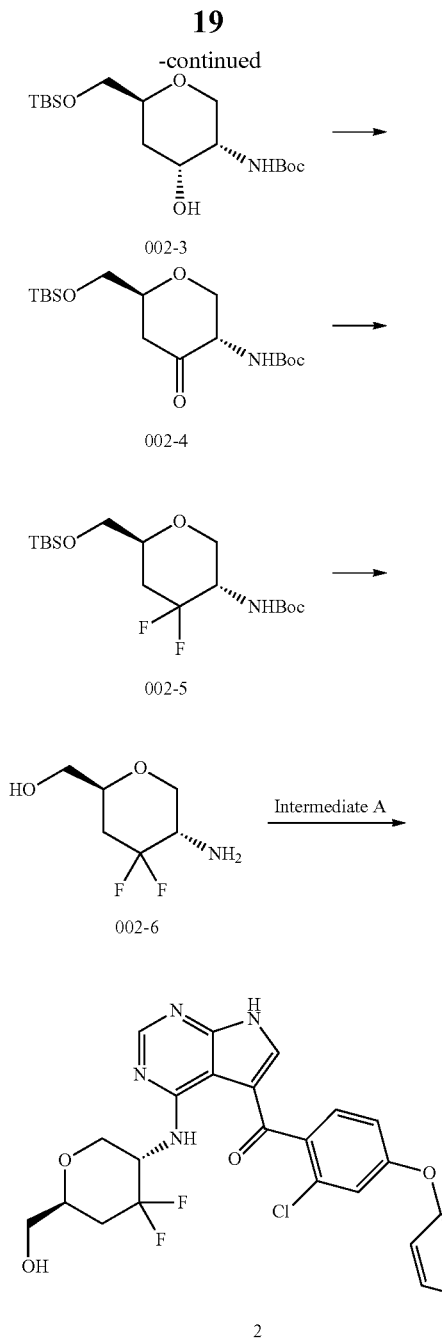

Step 1: Synthesis of Compound 002-2

Compound 001-1 (10 g, 29.11 mmol, 1 eq) was dissolved in dichloromethane (100 mL), and m-chloroperoxybenzoic acid (7.53 g, 43.66 mmol, 1.5 eq) was added at 0° C. The mixture was then reacted at 20° C. for 15 h. The reaction was quenched by adding saturated sodium sulfite solution to the reaction solution. Then the mixture was extracted with ethyl acetate (50 mL×3), washed with saturated brine, dried over anhydrous sodium sulfate, and concentrated to give a crude product. The crude product was purified by column chromatography (petroleum ether:ethyl acetate=10:1) to give compound 002-2. LCMS: (ESI) m/z: 304.2 [M-$^t$Bu+1].

Step 2: Synthesis of Compound 002-3

Compound 002-2 (5 g, 13.91 mmol, 1 eq) was dissolved in tetrahydrofuran (10 mL), and lithium aluminium hydride (2.5 M, 8.34 mL, 1.5 eq) was added at -20° C. After completion of the addition, the mixture was reacted at 20° C. for 3 h. After completion of the reaction, the reaction was quenched by adding sodium hydroxide solution to the reaction solution. The mixture was filtered. The filter cake was washed with ethyl acetate, and the filtrates were combined and concentrated to give a crude product. The crude product was purified by column chromatography (petroleum ether: ethyl acetate=3:1) to give compound 002-3. LCMS: (ESI) m/z: 306.1 [M-$^t$Bu+1].

Step 3: Synthesis of Compound 002-4

Compound 002-3 (1.7 g, 4.70 mmol, 1 eq) was dissolved in dichloromethane (3 mL), and Dess-Martin reagent (2.99 g, 7.05 mmol, 2.18 mL, 1.5 eq) was added at 0° C. After completion of the addition, the mixture was reacted at 20° C. for 3 h. The reaction solution was filtered, and the filtrate was rotary evaporated to dryness to give a crude product. The crude product was purified by column chromatography (petroleum ether:ethyl acetate=10:1) to give compound 002-4. LCMS: (ESI) m/z: 382.1 [M+Na].

Step 4: Synthesis of Compound 002-5

Compound 002-4 (0.21 g, 584.09 μmol, 1 eq) was dissolved in dichloroethane (10 mL), and diethylaminosulfur trifluoride (282.45 mg, 1.75 mmol, 231.51 μL, 3 eq) was added at -78° C. After completion of the addition, the mixture was reacted at 20° C. for 2 h. The reaction was quenched by adding saturated sodium bicarbonate solution to the reaction solution. Then the mixture was extracted with ethyl acetate (10 mL×3). The organic phase was washed with saturated brine, dried over anhydrous sodium sulfate, and filtered. The filtrate was concentrated to give a crude product. The crude product was purified by column chromatography (PE:EA=10:1) to give compound 002-5. LCMS: (ESI) m/z: 326.1 [M-$^t$Bu+1].

Step 5: Synthesis of Compound 002-6

Compound 002-5 (222.85 mg, 584.09 μmol, 1 eq) was dissolved in ethyl acetate (4 mL), and hydrochloric acid/ethyl acetate (584.09 μmol, 1 eq) was added. After completion of the addition, the reaction was reacted at 20° C. for 1 h. The reaction solution was rotary evaporated to dryness to give the crude compound 002-6, which was directly used in the next step. LCMS: (ESI) m/z: 168.1 [M+1].

Step 6: Synthesis of Compound 2

Compound 002-6 (97.63 mg, 584.09 μmol, 1 eq) and intermediate A (179.53 mg, 467.27 μmol, 0.8 eq) were dissolved in isopropanol (5 mL), and N,N-diisopropylethylamine (188.72 mg, 1.46 mmol, 254.34 μL, 2.5 eq) was added. The mixture was reacted with microwave at 130° C. for 2 h. The reaction solution was rotary evaporated to dryness to give a crude product. The crude product was purified by preparative separation (Column: Welch Xtimate C18 150 mm*25 mm*5 μm; Mobile phase: [water (0.225% formic acid)-acetonitrile]; B (acetonitrile) %: 40%-70%, 8.5 min) to give compound 2. LCMS: (ESI) m/z: 515.0 [M+1]. $^1$H NMR (400 MHz, CDCl$_3$) δ 9.39 (br d, J=8.4 Hz, 1H), 8.38 (br s, 1H), 7.39-7.53 (m, 4H), 7.21-7.27 (m, 1H), 7.12 (br d, J=8.8 Hz, 3H), 6.99 (br d, J=8.3 Hz, 1H), 5.03 (br s, 1H), 4.23-4.40 (m, 1H), 3.83 (br d, J=10.1 Hz, 2H), 3.54-3.73 (m, 2H), 2.06-2.24 ppm (m, 2H).

Example 3

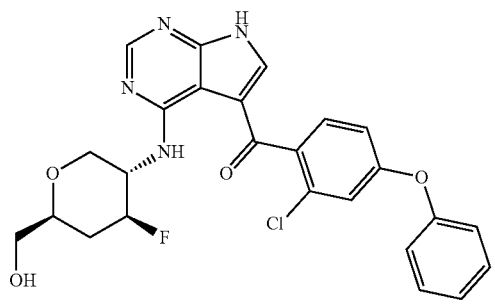

Route for Synthesis:

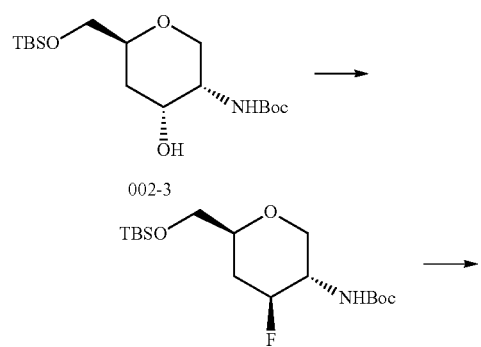

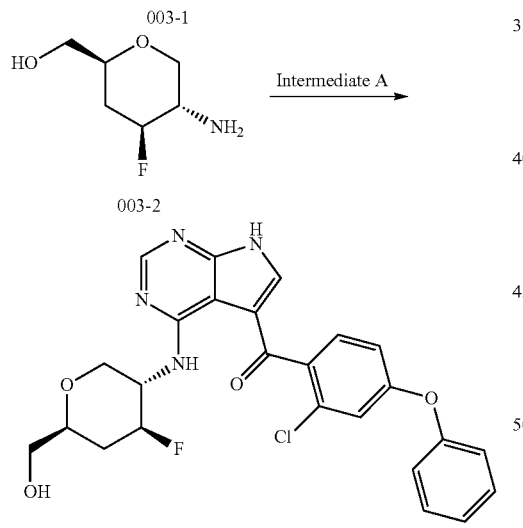

Step 1: Synthesis of Compound 003-1

Diethylaminosulfur trifluoride (249.66 mg, 1.55 mmol, 204.64 μL, 1.4 eq) was dissolved in dichloromethane (5 mL), and compound 002-3 (0.4 g, 1.11 mmol, 1 eq) was added at 0° C. After completion of the addition, the mixture was reacted at 0° C. for 1 h. Saturated ammonium chloride solution was added to the reaction solution. Then the mixture was extracted with ethyl acetate (10 mL×3). The organic phases were combined, washed with saturated brine, and dried over anhydrous sodium sulfate to give a crude product. The crude product was purified by column chromatography (petroleum ether:ethyl acetate=10:1) to give compound 003-1. LCMS: (ESI) m/z: 386.2 [M+Na].

Step 2: Synthesis of Compound 003-2

Compound 003-1 (0.12 g, 330.09 μmol, 1 eq) was dissolved in ethyl acetate (2 mL), and hydrochloric acid/ethyl acetate (4 M, 2.40 mL, 29.08 eq) was added under nitrogen. The mixture was reacted at 20° C. for 1 h. The reaction solution was rotary evaporated to dryness to give compound 003-2. Compound 003-2 was directly used in the next step without purification. LCMS: (ESI) m/z: 149.9 [M+H].

Step 3: Synthesis of Compound 3

Compound 003-2 (52.28 mg, 136.07 μmol, 0.8 eq) and intermediate A (25.37 mg, 170.09 μmol, 1 eq) was dissolved in isopropanol (5 mL), and N,N-dimethylformamide (54.96 mg, 425.23 μmol, 74.06 μL, 2.5 eq) was added. After completion of the addition, the mixture was reacted with microwave at 130° C. for 2 h. The reaction solution was rotary evaporated to dryness to give a crude product. The crude product was purified by preparative separation (Column: Welch Xtimate C18 150 mm*25 mm*5 μm; Mobile phase: [water (0.225% formic acid)-acetonitrile]; B (acetonitrile) %: 40%-70%, 8.5 min) to give compound 3. LCMS: (ESI) m/z: 497.1 [M+H]. $^1$H NMR (400 MHz, CDCl$_3$) δ 9.14 (br d, J=7.78 Hz, 1H), 8.38 (br s, 1H), 7.39-7.50 (m, 4H), 7.23-7.27 (m, 1H), 7.13 (br d, J=8.28 Hz, 3H), 6.99 (br d, J=8.28 Hz, 1H), 4.76-5.00 (m, 1H), 4.65 (br s, 1H), 4.33-4.50 (m, 1H), 3.73-3.84 (m, 1H), 3.64-3.73 (m, 2H), 3.37 (br t, J=11.04 Hz, 1H), 2.23-2.30 (m, 1H), 1.89 (br d, J=11.29 Hz, 1H).

Example 4

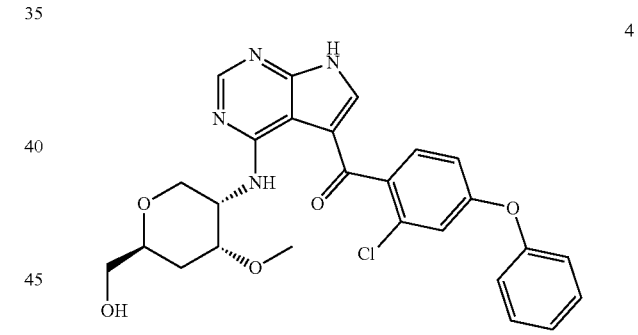

Route for Synthesis:

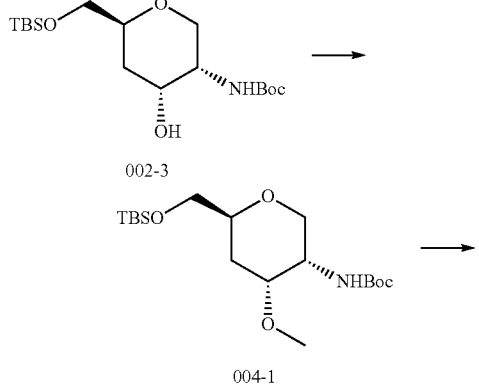

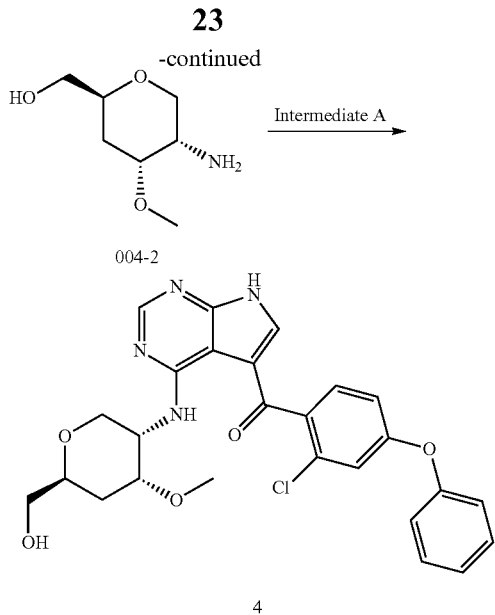

Step 1: Synthesis of Compound 004-1

Compound 002-3 (0.117 g, 323.61 µmol, 1 eq) was dissolved in acetonitrile (2 mL). Silver oxide (224.97 mg, 970.83 µmol, 3 eq) and iodomethane (459.33 mg, 3.24 mmol, 201.46 µL, 10 eq) were added sequentially at 20° C. under nitrogen. Then the mixture was heated to 80° C. for 12 hours. The reaction solution was cooled and then filtered, and the filtrate was rotary evaporated to dryness to give compound 004-1. Compound 004-1 was directly used in the next step without purification. LCMS: (ESI) m/z: 319.85 [M-$^t$Bu+].

Step 2: Synthesis of Compound 004-2

Compound 004-1 (121.54 mg, 323.61 µmol, 1 eq) was dissolved in dichloromethane (2 mL), and trifluoroacetic acid (30.80 mg, 270.12 µmol, 0.02 mL, 0.84 eq) was added. After completion of the addition, the mixture was reacted at 20° C. for 1 h. The reaction solution was directly rotary evaporated to dryness to give compound 004-2. Compound 004-2 was directly used in the next step without purification. LCMS: (ESI) m/z: 276.20 [M+H].

Step 3: Synthesis of Compound 4

Intermediate A (99.47 mg, 258.89 µmol, 0.8 eq) and compound 004-2 (89.14 mg, 323.61 µmol, 1 eq) were dissolved in isopropanol (2 mL), and N,N-diisopropylethylamine (104.56 mg, 809.03 µmol, 140.91 µL, 2.5 eq) was added. Then the mixture was reacted with microwave at 130° C. for 1 h. The reaction solution was rotary evaporated to dryness to give a crude product. The crude product was purified by preparative separation (Column Phenomenex Gemini-NX 80 mm*40 mm*3 µm; Mobile phase: [water (0.05% NH$_3$H$_2$O+10 mM NH$_4$HCO$_3$)-acetonitrile]; B (acetonitrile) %: 37%-57%, 8 min). LCMS: (ESI) m/z: 508.9 [M]. $^1$H NMR (400 MHz, CDCl$_3$) δ 9.25 (d, J=8.3 Hz, 1H), 8.35 (s, 1H), 7.50-7.39 (m, 3H), 7.39-7.32 (m, 1H), 7.28-7.22 (m, 1H), 7.14-7.08 (m, 3H), 6.98 (dd, J=2.3, 8.3 Hz, 1H), 4.57 (br d, J=5.5 Hz, 1H), 4.08 (dd, J=5.4, 10.2 Hz, 1H), 3.93-3.82 (m, 2H), 3.81-3.69 (m, 2H), 3.64-3.53 (m, 4H), 2.03 (br d, J=13.1 Hz, 1H), 1.70 (br s, 1H).

Single Crystal X-Ray Diffraction Detection and Analysis of Compound 4

Instrument Model: Bruker D8 Venture Photon II

Assay method: After being cultivated at room temperature for 5 days, a crystal of compound 4 was obtained by solvent volatilization method with acetone. The size of the crystal for diffraction was 0.07×0.15×0.34 mm. The crystal belonged to the triclinic system, and the space group was P1. The unit cell parameters were: a=9.3283(6), b=12.0149(7), c=12.7260(8) Å, α=98.952(3), β=106.257(2)°, γ=92.178(3)°. The unit cell volume V was 1347.59(15) Å$^3$ and the number of asymmetric units in the unit cell was Z=1.

Instrument Parameters:

The diffraction intensity data was collected using a Bruker D8 Venture Photon II diffractometer with a light source of CuK$_α$ radiation in a scanning mode of φ/ω scan, for a total of 31,231 diffraction points, 8,390 independent diffraction points and 8,135 observable points (I/sigma≥2).

The direct method (Shelxs97) was used to resolve the crystal structure and all 76 non-hydrogen atomic positions were obtained. The least squares method was used to correct the structural parameters and discriminate the atomic species. All hydrogen atomic positions were obtained using the geometric calculation method and the difference Fourier method. After refinement, R$_1$ was 0.0501, wR$_2$ was 0.1454 (w=1/σ|F|$^2$), and S was 1.046. The stoichiometric formula was determined finally to be (C$_{26}$H$_{25}$ClN$_4$O$_5$)$_2$·C$_3$H$_6$O, with a calculated molecular weight of 1075.97 and a calculated crystal density of 1.326 g/cm$^3$.

The result of single crystal shows that: the molecular arrangement in the crystalline state belongs to the first space group, the compound should have optical activity, the Flack coefficient is 0.049(4), and the absolute configuration of the compound in the crystal can be determined. In the crystalline state, there is hydrogen bond between molecules. Hydrogen bond and van der Waals force between molecules maintain the stable space arrangement of the molecules.

The ellipsoid diagram of the stereostructure of compound 4, the unit cell stacking diagram along the a-axis direction, and the absolute conformation diagram of the compound are shown in FIGS. 1, 2, 3 and 4. The crystal structure data and parameters of compound 4 are shown in Tables 1, 2, 3, 4 and 5.

TABLE 1

Crystal data of compound 4

| | |
|---|---|
| Empirical formula | C$_{55}$H$_{56}$Cl$_2$N$_8$O$_{11}$ |
| Formula weight | 1075.97 |
| Temperature | 160(2) K |
| Wavelength | 1.54178 A |
| Crystal system, space group | Triclinic, P1 |
| Unit cell dimensions | a = 9.3283(6) A alpha = 98.952(3) deg. |
| | b = 12.0149(7) A beta = 106.257(2) deg. |
| | c = 12.7260(8) A gamma = 92.178(3) deg. |
| Volume | 1347.59(15) A^3 |
| Z, Calculated density | 1, 1.326 Mg/m^3 |
| Absorption coefficient | 1.647 mm^-1 |

TABLE 1-continued

Crystal data of compound 4

| | |
|---|---|
| F(000) | 564 |
| Crystal size | 0.340 × 0.150 × 0.070 mm |
| Theta range for data collection | 3.673 to 65.174 deg. |
| Limiting indices | 10 <= h <= 10, −14 <= k <= 14, −13 <= l <= 14 |
| Reflections collected/unique | 31231/8390 [R(int) = 0.0321] |
| Completeness to theta = 65.174 | 98.8% |
| Absorption correction | None |
| Refinement method | Full-matrix least-squares on F^2 |
| Data/restraints/parameters | 8390/3/686 |
| Goodness-of-fit on F^2 | 1.046 |
| Final R indices [I > 2sigma(I)] | R1 = 0.0501, wR2 = 0.1410 |
| R indices (all data) | R1 = 0.0534, wR2 = 0.1454 |
| Absolute structure parameter | 0.049(4) |
| Extinction coefficient | 0.0051(10) |
| Largest diff. peak and hole | 0.757 and −0.384 e · A^−3 |

TABLE 2

Atomic coordinates (×10$^4$) and equivalent isotropic shift parameters (Å$^2$ × 10$^3$) of compound 4 crystal

| | x | y | z | U(eq) |
|---|---|---|---|---|
| Cl(1) | 11051 (1) | 4517 (1) | 3711 (1) | 49 (1) |
| Cl(2) | −1088 (2) | 6045 (2) | 5683 (1) | 76 (1) |
| O(1) | 8170 (4) | 4316 (3) | 1068 (3) | 37 (1) |
| O(1') | 4841 (11) | 8377 (6) | 5379 (7) | 129 (3) |
| O(2) | 11724 (4) | 374 (3) | 3135 (3) | 47 (1) |
| O(3) | 6405 (3) | 9105 (2) | 303 (2) | 35 (1) |
| O(4) | 7619 (4) | 6483 (3) | −619 (3) | 39 (1) |
| O(5) | 4674 (5) | 10032 (3) | −1511 (3) | 55 (1) |
| O(6) | 1746 (5) | 5922 (4) | 8522 (3) | 61 (1) |
| O(7) | −1555 (8) | 10136 (5) | 7106 (10) | 164 (5) |
| O(8) | 4995 (3) | 1933 (3) | 10182 (3) | 38 (1) |
| O(9) | 2682 (4) | 4088 (3) | 10320 (3) | 45 (1) |
| O(10) | 3846 (5) | −29 (3) | 10801 (4) | 59 (1) |
| N(1) | 6035 (4) | 4348 (3) | 3919 (3) | 35 (1) |
| N(2) | 4912 (4) | 6869 (3) | 2168 (3) | 38 (1) |
| N(3) | 4648 (4) | 5990 (3) | 3673 (3) | 37 (1) |
| N(4) | 6338 (4) | 6222 (3) | 1019 (3) | 32 (1) |
| N(5) | 3766 (4) | 5890 (3) | 5615 (3) | 31 (1) |
| N(6) | 4345 (5) | 3101 (3) | 7062 (3) | 40 (1) |
| N(7) | 4824 (4) | 4092 (3) | 5671 (3) | 35 (1) |
| N(8) | 3141 (4) | 3868 (3) | 8323 (3) | 37 (1) |
| C(1) | 6982 (5) | 3795 (4) | 3439 (4) | 31 (1) |
| C(1') | 3850 (17) | 10099 (9) | 5806 (9) | 129 (4) |
| C(2) | 7153 (4) | 4297 (3) | 2563 (3) | 28 (1) |
| C(2') | 4700 (11) | 9331 (8) | 5226 (7) | 89 (2) |
| C(3) | 6233 (4) | 5236 (3) | 2522 (4) | 28 (1) |
| C(3') | 5371 (12) | 9809 (10) | 4521 (10) | 114 (3) |
| C(4) | 5833 (5) | 6108 (3) | 1886 (4) | 31 (1) |
| C(5) | 4393 (5) | 6763 (4) | 3027 (4) | 39 (1) |
| C(6) | 5580 (5) | 5240 (4) | 3386 (4) | 31 (1) |
| C(7) | 8103 (4) | 3907 (3) | 1888 (3) | 28 (1) |
| C(8) | 9046 (5) | 2952 (3) | 2205 (4) | 28 (1) |
| C(9) | 10407 (5) | 3149 (3) | 3020 (4) | 30 (1) |
| C(10) | 11309 (5) | 2282 (4) | 3312 (4) | 35 (1) |
| C(11) | 10784 (5) | 1188 (4) | 2779 (4) | 33 (1) |
| C(12) | 9427 (5) | 956 (4) | 1970 (4) | 36 (1) |
| C(13) | 8582 (5) | 1841 (4) | 1681 (4) | 33 (1) |
| C(14) | 11201 (5) | −768 (4) | 2774 (4) | 40 (1) |
| C(15) | 11412 (5) | −1317 (4) | 1809 (4) | 41 (1) |
| C(16) | 10932 (5) | −2466 (4) | 1468 (5) | 45 (1) |
| C(17) | 10295 (5) | −3037 (4) | 2099 (5) | 45 (1) |
| C(18) | 10140 (7) | −2469 (5) | 3094 (5) | 54 (1) |
| C(19) | 10584 (7) | −1321 (5) | 3432 (5) | 52 (1) |
| C(20) | 5919 (5) | 7117 (4) | 372 (4) | 31 (1) |
| C(21) | 6109 (5) | 6769 (4) | −777 (4) | 33 (1) |
| C(22) | 5777 (5) | 7757 (4) | −1415 (4) | 38 (1) |
| C(23) | 6658 (5) | 8847 (5) | −770 (4) | 37 (1) |
| C(24) | 6844 (5) | 8235 (4) | 953 (4) | 33 (1) |
| C(25) | 7822 (8) | 5723 (6) | −1521 (6) | 65 (2) |
| C(26) | 6199 (7) | 9852 (5) | −1352 (5) | 51 (1) |
| C(27) | 2878 (5) | 6482 (4) | 6141 (4) | 34 (1) |
| C(28) | 2599 (5) | 5914 (4) | 6943 (4) | 32 (1) |

TABLE 2-continued

Atomic coordinates (×10$^4$) and equivalent isotropic shift parameters (Å$^2$ × 10$^3$) of compound 4 crystal

| | x | y | z | U(eq) |
|---|---|---|---|---|
| C(29) | 3381 (5) | 4897 (4) | 6885 (3) | 30 (1) |
| C(30) | 3612 (5) | 3961 (4) | 7441 (4) | 34 (1) |
| C(31) | 4879 (5) | 3228 (4) | 6205 (4) | 40 (1) |
| C(32) | 4045 (4) | 4919 (4) | 6047 (4) | 31 (1) |
| C(33) | 1739 (5) | 6328 (4) | 7700 (4) | 40 (1) |
| C(34) | 868 (5) | 7334 (4) | 7473 (5) | 44 (1) |
| C(35) | −412 (6) | 7302 (4) | 6594 (5) | 47 (1) |
| C(36) | −1241 (8) | 8220 (6) | 6436 (7) | 70 (2) |
| C(37) | −732 (10) | 9211 (6) | 7196 (11) | 103 (4) |
| C(38) | 522 (11) | 9273 (6) | 8098 (13) | 136 (6) |
| C(39) | 1318 (8) | 8320 (6) | 8236 (10) | 106 (4) |
| C(40) | −1015 (8) | 11069 (5) | 6800 (7) | 73 (2) |
| C(41) | −1621 (7) | 12036 (5) | 7069 (5) | 57 (1) |
| C(42) | −1188 (8) | 13009 (5) | 6724 (7) | 78 (2) |
| C(43) | −131 (8) | 12960 (7) | 6131 (7) | 74 (2) |
| C(44) | 529 (10) | 11983 (7) | 5948 (7) | 84 (2) |
| C(45) | 110 (10) | 11041 (6) | 6299 (9) | 95 (3) |
| C(46) | 3285 (5) | 2902 (4) | 8880 (4) | 33 (1) |
| C(47) | 2258 (5) | 3014 (4) | 9634 (4) | 38 (1) |
| C(48) | 2453 (5) | 2051 (4) | 10313 (4) | 40 (1) |
| C(49) | 4087 (5) | 2011 (4) | 10941 (4) | 35 (1) |
| C(50) | 4885 (5) | 2874 (4) | 9600 (4) | 37 (1) |
| C(51) | 1633 (10) | 4504 (7) | 10855 (8) | 85 (2) |
| C(52) | 4362 (6) | 1010 (5) | 11533 (5) | 50 (1) |
| H(5A) | 4599 | 10591 | −1048 | 82 |
| H(10A) | 4528 | −259 | 10531 | 88 |
| H(1A) | 5754 | 4169 | 4481 | 41 |
| H(4A) | 6945 | 5736 | 832 | 39 |
| H(5B) | 4104 | 6096 | 5088 | 37 |
| H(8A) | 2708 | 4441 | 8586 | 44 |
| H(1B) | 7464 | 3154 | 3667 | 38 |
| H(1'A) | 3863 | 10837 | 5570 | 193 |
| H(1'B) | 2811 | 9775 | 5622 | 193 |
| H(1'C) | 4313 | 10193 | 6611 | 193 |
| H(3'A) | 5116 | 10592 | 4513 | 171 |
| H(3'B) | 6461 | 9797 | 4792 | 171 |
| H(3'C) | 5003 | 9372 | 3767 | 171 |
| H(5C) | 3755 | 7318 | 3196 | 47 |
| H(10B) | 12255 | 2438 | 3860 | 42 |
| H(12A) | 9076 | 200 | 1616 | 43 |
| H(13A) | 7658 | 1686 | 1109 | 39 |
| H(15A) | 11875 | −925 | 1380 | 49 |
| H(16A) | 11048 | −2855 | 791 | 54 |
| H(17A) | 9962 | −3816 | 1858 | 54 |
| H(18A) | 9727 | −2867 | 3545 | 65 |
| H(19A) | 10465 | −927 | 4106 | 62 |
| H(20A) | 4838 | 7228 | 288 | 37 |
| H(21A) | 5400 | 6095 | −1185 | 39 |
| H(22A) | 6019 | 7569 | −2127 | 46 |
| H(22B) | 4693 | 7863 | −1587 | 46 |
| H(23A) | 7749 | 8770 | −669 | 45 |
| H(24A) | 6693 | 8458 | 1694 | 40 |

TABLE 2-continued

Atomic coordinates (×10⁴) and equivalent isotropic shift parameters (Å² × 10³) of compound 4 crystal

|        | x     | y     | z     | U(eq) |
|--------|-------|-------|-------|-------|
| H(24B) | 7922  | 8138  | 1060  | 40    |
| H(25A) | 8876  | 5563  | −1360 | 98    |
| H(25B) | 7192  | 5017  | −1635 | 98    |
| H(25C) | 7536  | 6061  | −2195 | 98    |
| H(26A) | 6821  | 10541 | −905  | 61    |
| H(26B) | 6398  | 9720  | −2084 | 61    |
| H(27A) | 2504  | 7181  | 5983  | 41    |
| H(31A) | 5365  | 2607  | 5947  | 48    |
| H(36A) | −2124 | 8176  | 5831  | 84    |
| H(38A) | 840   | 9956  | 8618  | 163   |
| H(39A) | 2174  | 8351  | 8859  | 127   |
| H(41A) | −2325 | 12054 | 7484  | 68    |
| H(42A) | −1608 | 13699 | 6890  | 94    |
| H(43A) | 128   | 13607 | 5855  | 89    |
| H(44A) | 1282  | 11959 | 5575  | 101   |
| H(45A) | 595   | 10368 | 6198  | 114   |
| H(46A) | 2975  | 2190  | 8321  | 40    |
| H(47A) | 1191  | 2981  | 9172  | 46    |
| H(48A) | 1855  | 2164  | 10846 | 48    |
| H(48B) | 2076  | 1321  | 9808  | 48    |
| H(49A) | 4429  | 2722  | 11501 | 42    |
| H(50A) | 5569  | 2809  | 9127  | 44    |
| H(50B) | 5193  | 3588  | 10143 | 44    |
| H(51A) | 2022  | 5248  | 11308 | 128   |
| H(51B) | 689   | 4574  | 10297 | 128   |
| H(51C) | 1455  | 3980  | 11333 | 128   |
| H(52A) | 5450  | 1013  | 11897 | 60    |
| H(52B) | 3848  | 1081  | 12120 | 60    |

TABLE 3

Bond length (Å) and bond angle (°) of compound 4

| | | | |
|---|---|---|---|
| Cl(1)—C(9) | 1.736(4) | O(7)—C(40) | 1.365(8) |
| Cl(2)—C(35) | 1.731(6) | O(7)—C(37) | 1.376(8) |
| O(1)—C(7) | 1.237(5) | O(8)—C(50) | 1.436(5) |
| O(1')—C(2') | 1.198(11) | O(8)—C(49) | 1.448(5) |
| O(2)—C(11) | 1.383(5) | O(9)—C(51) | 1.406(7) |
| O(2)—C(14) | 1.399(6) | O(9)—C(47) | 1.415(6) |
| O(3)—C(24) | 1.435(5) | O(10)—C(52) | 1.414(8) |
| O(3)—C(23) | 1.438(6) | O(10)—H(10A) | 0.8400 |
| O(4)—C(25) | 1.414(6) | N(1)—C(1) | 1.348(6) |
| O(4)—C(21) | 1.429(5) | N(1)—C(6) | 1.373(6) |
| O(5)—C(26) | 1.409(7) | N(1)—H(1A) | 0.8800 |
| O(5)—H(5A) | 0.8400 | N(2)—C(5) | 1.335(6) |
| O(6)—C(33) | 1.220(7) | N(2)—C(4) | 1.353(6) |
| N(3)—C(5) | 1.320(6) | C(16)—C(17) | 1.369(8) |
| N(3)—C(6) | 1.355(6) | C(16)—H(16A) | 0.9500 |
| N(4)—C(4) | 1.339(6) | C(17)—C(18) | 1.390(9) |
| N(4)—C(20) | 1.454(5) | C(17)—H(17A) | 0.9500 |
| N(4)—H(4A) | 0.8800 | C(18)—C(19) | 1.390(8) |
| N(5)—C(27) | 1.358(6) | C(18)—H(18A) | 0.9500 |
| N(5)—C(32) | 1.369(6) | C(19)—H(19A) | 0.9500 |
| N(5)—H(5B) | 0.8800 | C(20)—C(21) | 1.518(6) |
| N(6)—C(31) | 1.346(6) | C(20)—C(24) | 1.530(6) |
| N(6)—C(30) | 1.360(6) | C(20)—H(20A) | 1.0000 |
| N(7)—C(31) | 1.321(6) | C(21)—C(22) | 1.533(6) |
| N(7)—C(32) | 1.360(6) | C(21)—H(21A) | 1.0000 |
| N(8)—C(30) | 1.334(6) | C(22)—C(23) | 1.506(7) |
| N(8)—C(46) | 1.443(6) | C(22)—H(22A) | 0.9900 |
| N(8)—H(8A) | 0.8800 | C(22)—H(22B) | 0.9900 |
| C(1)—C(2) | 1.390(6) | C(23)—C(26) | 1.526(7) |
| C(1)—H(1B) | 0.9500 | C(23)—H(23A) | 1.0000 |
| C(1')—C(2') | 1.483(15) | C(24)—H(24A) | 0.9900 |
| C(1')—H(1'A) | 0.9800 | C(24)—H(24B) | 0.9900 |
| C(1')—H(1'B) | 0.9800 | C(25)—H(25A) | 0.9800 |
| C(1')—H(1'C) | 0.9800 | C(25)—H(25B) | 0.9800 |
| C(2)—C(7) | 1.441(6) | C(25)—H(25C) | 0.9800 |
| C(2)—C(3) | 1.442(6) | C(26)—H(26A) | 0.9900 |
| C(2')—C(3') | 1.405(13) | C(26)—H(26B) | 0.9900 |
| C(3)—C(6) | 1.397(6) | C(27)—C(28) | 1.389(7) |
| C(3)—C(4) | 1.421(6) | C(27)—H(27A) | 0.9500 |
| C(3')—H(3'A) | 0.9800 | C(28)—C(29) | 1.449(6) |
| C(3')—H(3'B) | 0.9800 | C(28)—C(33) | 1.460(6) |
| C(3')—H(3'C) | 0.9800 | C(29)—C(32) | 1.378(6) |
| C(5)—H(5C) | 0.9500 | C(29)—C(30) | 1.411(6) |
| C(7)—C(8) | 1.508(6) | C(31)—H(31A) | 0.9500 |
| C(8)—C(9) | 1.382(6) | C(33)—C(34) | 1.503(7) |
| C(8)—C(13) | 1.389(6) | C(34)—C(39) | 1.378(8) |
| C(9)—C(10) | 1.393(6) | C(34)—C(35) | 1.384(8) |
| C(10)—C(11) | 1.384(6) | C(35)—C(36) | 1.379(8) |
| C(10)—H(10B) | 0.9500 | C(36)—C(37) | 1.385(13) |
| C(11)—C(12) | 1.377(6) | C(36)—H(36A) | 0.9500 |
| C(12)—C(13) | 1.382(6) | C(37)—C(38) | 1.381(17) |
| C(12)—H(12A) | 0.9500 | C(38)—C(39) | 1.395(13) |
| C(13)—H(13A) | 0.9500 | C(38)—H(38A) | 0.9500 |

TABLE 3-continued

| Bond length (Å) and bond angle (°) of compound 4 | | | |
|---|---|---|---|
| C(14)—C(15) | 1.370(7) | C(39)—H(39A) | 0.9500 |
| C(14)—C(19) | 1.374(8) | C(40)—C(41) | 1.350(8) |
| C(15)—C(16) | 1.398(7) | C(40)—C(45) | 1.371(10) |
| C(15)—H(15A) | 0.9500 | C(41)—C(42) | 1.395(10) |
| C(41)—H(41A) | 0.9500 | C(31)—N(6)—C(30) | 117.2(4) |
| C(42)—C(43) | 1.397(12) | C(31)—N(7)—C(32) | 111.9(4) |
| C(42)—H(42A) | 0.9500 | C(30)—N(8)—C(46) | 125.1(4) |
| C(43)—C(44) | 1.365(12) | C(30)—N(8)—H(8A) | 117.4 |
| C(43)—H(43A) | 0.9500 | C(46)—N(8)—H(8A) | 117.4 |
| C(44)—C(45) | 1.362(12) | N(1)—C(1)—C(2) | 110.3(4) |
| C(44)—H(44A) | 0.9500 | N(1)—C(1)—H(1B) | 124.8 |
| C(45)—H(45A) | 0.9500 | C(2)—C(1)—H(1B) | 124.8 |
| C(46)—C(50) | 1.521(6) | C(2')—C(1')—H(1'A) | 109.5 |
| C(46)—C(47) | 1.531(6) | C(2')—C(1')—H(1'B) | 109.5 |
| C(46)—H(46A) | 1.0000 | H(1'A)—C(1')—H(1'B) | 109.5 |
| C(47)—C(48) | 1.534(6) | C(2')—C(1')—H(1'C) | 109.5 |
| C(47)—H(47A) | 1.0000 | H(1'A)—C(1')—H(1'C) | 109.5 |
| C(48)—C(49) | 1.516(6) | H(1'B)—C(1')—H(1'C) | 109.5 |
| C(48)—H(48A) | 0.9900 | C(1)—C(2)—C(7) | 123.8(4) |
| C(48)—H(48B) | 0.9900 | C(1)—C(2)—C(3) | 105.9(4) |
| C(49)—C(52) | 1.509(7) | C(7)—C(2)—C(3) | 130.3(4) |
| C(49)—H(49A) | 1.0000 | O(1')—C(2')—C(3') | 122.5(10) |
| C(50)—H(50A) | 0.9900 | O(1')—C(2')—C(1') | 121.8(10) |
| C(50)—H(50B) | 0.9900 | C(3')—C(2')—C(1') | 115.6(10) |
| C(51)—H(51A) | 0.9800 | C(6)—C(3)—C(4) | 114.9(4) |
| C(51)—H(51B) | 0.9800 | C(6)—C(3)—C(2) | 106.1(4) |
| C(51)—H(51C) | 0.9800 | C(4)—C(3)—C(2) | 139.0(4) |
| C(52)—H(52A) | 0.9900 | C(2')—C(3')—H(3'A) | 109.5 |
| C(52)—H(52B) | 0.9900 | C(2')—C(3')—H(3'B) | 109.5 |
| C(11)—O(2)—C(14) | 118.9(3) | H(3'A)—C(3')—H(3'B) | 109.5 |
| C(24)—O(3)—C(23) | 112.1(3) | C(2')—C(3')—H(3'C) | 109.5 |
| C(25)—O(4)—C(21) | 113.6(4) | H(3'A)—C(3')—H(3'C) | 109.5 |
| C(26)—O(5)—H(5A) | 109.5 | H(3'B)—C(3')—H(3'C) | 109.5 |
| C(40)—O(7)—C(37) | 119.9(5) | N(4)—C(4)—N(2) | 118.0(4) |
| C(50)—O(8)—C(49) | 112.4(3) | N(4)—C(4)—C(3) | 122.9(4) |
| C(51)—O(9)—C(47) | 115.3(5) | N(2)—C(4)—C(3) | 119.1(4) |
| C(52)—O(10)—H(10A) | 109.5 | N(3)—C(5)—N(2) | 128.6(4) |
| C(1)—N(1)—C(6) | 108.6(4) | N(3)—C(5)—H(5C) | 115.7 |
| C(1)—N(1)—H(1A) | 125.7 | N(2)—C(5)—H(5C) | 115.7 |
| C(6)—N(1)—H(1A) | 125.7 | N(3)—C(6)—N(1) | 124.2(4) |
| C(5)—N(2)—C(4) | 118.7(4) | N(3)—C(6)—C(3) | 126.7(4) |
| C(5)—N(3)—C(6) | 112.0(4) | N(1)—C(6)—C(3) | 109.0(4) |
| C(4)—N(4)—C(20) | 122.4(3) | O(1)—C(7)—C(2) | 123.0(4) |
| C(4)—N(4)—H(4A) | 118.8 | O(1)—C(7)—C(8) | 119.3(4) |
| C(20)—N(4)—H(4A) | 118.8 | C(2)—C(7)—C(8) | 117.8(4) |
| C(27)—N(5)—C(32) | 108.2(4) | C(9)—C(8)—C(13) | 117.5(4) |
| C(27)—N(5)—H(5B) | 125.9 | C(9)—C(8)—C(7) | 121.3(4) |
| C(32)—N(5)—H(5B) | 125.9 | C(13)—C(8)—C(7) | 121.2(4) |
| C(8)—C(9)—C(10) | 122.2(4) | C(22)—C(21)—H(21A) | 109.7 |
| C(8)—C(9)—Cl(1) | 119.9(3) | C(23)—C(22)—C(21) | 112.5(4) |
| C(10)—C(9)—Cl(1) | 117.9(3) | C(23)—C(22)—H(22A) | 109.1 |
| C(11)—C(10)—C(9) | 118.0(4) | C(21)—C(22)—H(22A) | 109.1 |
| C(11)—C(10)—H(10B) | 121.0 | C(23)—C(22)—H(22B) | 109.1 |
| C(9)—C(10)—H(10B) | 121.0 | C(21)—C(22)—H(22B) | 109.1 |
| C(12)—C(11)—O(2) | 124.0(4) | H(22A)—C(22)—H(22B) | 107.8 |
| C(12)—C(11)—C(10) | 121.4(4) | O(3)—C(23)—C(22) | 110.4(3) |
| O(2)—C(11)—C(10) | 114.5(4) | O(3)—C(23)—C(26) | 106.6(4) |
| C(11)—C(12)—C(13) | 118.9(4) | C(22)—C(23)—C(26) | 112.2(4) |
| C(11)—C(12)—H(12A) | 120.5 | O(3)—C(23)—H(23A) | 109.2 |
| C(13)—C(12)—H(12A) | 120.5 | C(22)—C(23)—H(23A) | 109.2 |
| C(12)—C(13)—C(8) | 121.8(4) | C(26)—C(23)—H(23A) | 109.2 |
| C(12)—C(13)—H(13A) | 119.1 | O(3)—C(24)—C(20) | 110.3(3) |
| C(8)—C(13)—H(13A) | 119.1 | O(3)—C(24)—H(24A) | 109.6 |
| C(15)—C(14)—C(19) | 122.0(5) | C(20)—C(24)—H(24A) | 109.6 |
| C(15)—C(14)—O(2) | 118.6(4) | O(3)—C(24)—H(24B) | 109.6 |
| C(19)—C(14)—O(2) | 119.2(5) | C(20)—C(24)—H(24B) | 109.6 |
| C(14)—C(15)—C(16) | 118.6(4) | H(24A)—C(24)—H(24B) | 108.1 |
| C(14)—C(15)—H(15A) | 120.7 | O(4)—C(25)—H(25A) | 109.5 |
| C(16)—C(15)—H(15A) | 120.7 | O(4)—C(25)—H(25B) | 109.5 |
| C(17)—C(16)—C(15) | 120.7(5) | H(25A)—C(25)—H(25B) | 109.5 |
| C(17)—C(16)—H(16A) | 119.7 | O(4)—C(25)—H(25C) | 109.5 |
| C(15)—C(16)—H(16A) | 119.7 | H(25A)—C(25)—H(25C) | 109.5 |
| C(16)—C(17)—C(18) | 119.6(5) | H(25B)—C(25)—H(25C) | 109.5 |
| C(16)—C(17)—H(17A) | 120.2 | O(5)—C(26)—C(23) | 112.8(4) |
| C(18)—C(17)—H(17A) | 120.2 | O(5)—C(26)—H(26A) | 109.0 |
| C(19)—C(18)—C(17) | 120.4(5) | C(23)—C(26)—H(26A) | 109.0 |
| C(19)—C(18)—H(18A) | 119.8 | O(5)—C(26)—H(26B) | 109.0 |
| C(17)—C(18)—H(18A) | 119.8 | C(23)—C(26)—H(26B) | 109.0 |

TABLE 3-continued

Bond length (Å) and bond angle (°) of compound 4

| | | | |
|---|---|---|---|
| C(14)—C(19)—C(18) | 118.7(5) | H(26A)—C(26)—H(26B) | 107.8 |
| C(14)—C(19)—H(19A) | 120.7 | N(5)—C(27)—C(28) | 109.9(4) |
| C(18)—C(19)—H(19A) | 120.7 | N(5)—C(27)—H(27A) | 125.0 |
| N(4)—C(20)—C(21) | 109.6(3) | C(28)—C(27)—H(27A) | 125.0 |
| N(4)—C(20)—C(24) | 111.4(3) | C(27)—C(28)—C(29) | 105.8(4) |
| C(21)—C(20)—C(24) | 110.5(4) | C(27)—C(28)—C(33) | 124.9(4) |
| N(4)—C(20)—H(20A) | 108.4 | C(29)—C(28)—C(33) | 129.3(4) |
| C(21)—C(20)—H(20A) | 108.4 | C(32)—C(29)—C(30) | 116.6(4) |
| C(24)—C(20)—H(20A) | 108.4 | C(32)—C(29)—C(28) | 106.1(4) |
| O(4)—C(21)—C(20) | 106.7(3) | C(30)—C(29)—C(28) | 137.3(4) |
| O(4)—C(21)—C(22) | 111.9(4) | N(8)—C(30)—N(6) | 117.7(4) |
| C(20)—C(21)—C(22) | 108.9(3) | N(8)—C(30)—C(29) | 123.3(4) |
| O(4)—C(21)—H(21A) | 109.7 | N(6)—C(30)—C(29) | 119.0(4) |
| C(20)—C(21)—H(21A) | 109.7 | N(7)—C(31)—N(6) | 129.3(4) |
| N(7)—C(31)—H(31A) | 115.4 | C(40)—C(45)—H(45A) | 120.2 |
| N(6)—C(31)—H(31A) | 115.4 | N(8)—C(46)—C(50) | 111.2(4) |
| N(7)—C(32)—N(5) | 124.3(4) | N(8)—C(46)—C(47) | 107.5(4) |
| N(7)—C(32)—C(29) | 125.7(4) | C(50)—C(46)—C(47) | 108.4(4) |
| N(5)—C(32)—C(29) | 109.9(4) | N(8)—C(46)—H(46A) | 109.9 |
| O(6)—C(33)—C(28) | 123.0(5) | C(50)—C(46)—H(46A) | 109.9 |
| O(6)—C(33)—C(34) | 119.1(4) | C(47)—C(46)—H(46A) | 109.9 |
| C(28)—C(33)—C(34) | 117.8(4) | O(9)—C(47)—C(46) | 105.9(3) |
| C(39)—C(34)—C(35) | 118.5(6) | O(9)—C(47)—C(48) | 112.1(4) |
| C(39)—C(34)—C(33) | 117.4(6) | C(46)—C(47)—C(48) | 109.8(4) |
| C(35)—C(34)—C(33) | 123.9(4) | O(9)—C(47)—H(47A) | 109.7 |
| C(36)—C(35)—C(34) | 122.9(6) | C(46)—C(47)—H(47A) | 109.7 |
| C(36)—C(35)—Cl(2) | 117.4(5) | C(48)—C(47)—H(47A) | 109.7 |
| C(34)—C(35)—Cl(2) | 119.6(4) | C(49)—C(48)—C(47) | 110.9(4) |
| C(35)—C(36)—C(37) | 117.2(8) | C(49)—C(48)—H(48A) | 109.4 |
| C(35)—C(36)—H(36A) | 121.4 | C(47)—C(48)—H(48A) | 109.4 |
| C(37)—C(36)—H(36A) | 121.4 | C(49)—C(48)—H(48B) | 109.4 |
| O(7)—C(37)—C(38) | 118.5(9) | C(47)—C(48)—H(48B) | 109.4 |
| O(7)—C(37)—C(36) | 119.5(10) | H(48A)—C(48)—H(48B) | 108.0 |
| C(38)—C(37)—C(36) | 121.8(6) | O(8)—C(49)—C(52) | 106.9(4) |
| C(37)—C(38)—C(39) | 119.2(7) | O(8)—C(49)—C(48) | 110.2(4) |
| C(37)—C(38)—H(38A) | 120.4 | C(52)—C(49)—C(48) | 113.1(4) |
| C(39)—C(38)—H(38A) | 120.4 | O(8)—C(49)—H(49A) | 108.8 |
| C(34)—C(39)—C(38) | 120.4(9) | C(52)—C(49)—H(49A) | 108.8 |
| C(34)—C(39)—H(39A) | 119.8 | C(48)—C(49)—H(49A) | 108.8 |
| C(38)—C(39)—H(39A) | 119.8 | O(8)—C(50)—C(46) | 110.5(4) |
| C(41)—C(40)—O(7) | 115.3(6) | O(8)—C(50)—H(50A) | 109.6 |
| C(41)—C(40)—C(45) | 122.1(6) | C(46)—C(50)—H(50A) | 109.6 |
| O(7)—C(40)—C(45) | 122.6(6) | O(8)—C(50)—H(50B) | 109.6 |
| C(40)—C(41)—C(42) | 118.4(6) | C(46)—C(50)—H(50B) | 109.6 |
| C(40)—C(41)—H(41A) | 120.8 | H(50A)—C(50)—H(50B) | 108.1 |
| C(42)—C(41)—H(41A) | 120.8 | O(9)—C(51)—H(51A) | 109.5 |
| C(41)—C(42)—C(43) | 119.5(6) | O(9)—C(51)—H(51B) | 109.5 |
| C(41)—C(42)—H(42A) | 120.3 | H(51A)—C(51)—H(51B) | 109.5 |
| C(43)—C(42)—H(42A) | 120.3 | O(9)—C(51)—H(51C) | 109.5 |
| C(44)—C(43)—C(42) | 119.9(6) | H(51A)—C(51)—H(51C) | 109.5 |
| C(44)—C(43)—H(43A) | 120.1 | H(51B)—C(51)—H(51C) | 109.5 |
| C(42)—C(43)—H(43A) | 120.1 | O(10)—C(52)—C(49) | 112.2(4) |
| C(45)—C(44)—C(43) | 120.1(7) | O(10)—C(52)—H(52A) | 109.2 |
| C(45)—C(44)—H(44A) | 120.0 | C(49)—C(52)—H(52A) | 109.2 |
| C(43)—C(44)—H(44A) | 120.0 | O(10)—C(52)—H(52B) | 109.2 |
| C(44)—C(45)—C(40) | 119.6(7) | C(49)—C(52)—H(52B) | 109.2 |
| C(44)—C(45)—H(45A) | 120.2 | H(52A)—C(52)—H(52B) | 107.9 |

TABLE 4

Twist angle (°) of compound 4

| | |
|---|---|
| C(6)—N(1)—C(1)—C(2) | −1.1(5) |
| N(1)—C(1)—C(2)—C(7) | 179.5(4) |
| N(1)—C(1)—C(2)—C(3) | 0.4(5) |
| C(1)—C(2)—C(3)—C(6) | 0.5(4) |
| C(7)—C(2)—C(3)—C(6) | −178.6(4) |
| C(1)—C(2)—C(3)—C(4) | −179.7(5) |
| C(7)—C(2)—C(3)—C(4) | 1.2(8) |
| C(20)—N(4)—C(4)—N(2) | −0.6(6) |
| C(20)—N(4)—C(4)—C(3) | 179.9(4) |
| C(5)—N(2)—C(4)—N(4) | 179.6(4) |
| C(5)—N(2)—C(4)—C(3) | −0.9(6) |
| C(6)—C(3)—C(4)—N(4) | −179.0(4) |
| C(2)—C(3)—C(4)—N(4) | 1.2(8) |
| C(6)—C(3)—C(4)—N(2) | 1.5(6) |
| C(2)—C(3)—C(4)—N(2) | −178.3(5) |
| C(6)—N(3)—C(5)—N(2) | 0.7(7) |
| C(4)—N(2)—C(5)—N(3) | −0.3(8) |
| C(5)—N(3)—C(6)—N(1) | 179.9(4) |
| C(5)—N(3)—C(6)—C(3) | 0.1(7) |
| C(1)—N(1)—C(6)—N(3) | −178.5(4) |
| C(1)—N(1)—C(6)—C(3) | 1.4(5) |
| C(4)—C(3)—C(6)—N(3) | −1.1(6) |
| C(2)—C(3)—C(6)—N(3) | 178.7(4) |
| C(4)—C(3)—C(6)—N(1) | 179.0(3) |
| C(2)—C(3)—C(6)—N(1) | −1.2(5) |
| C(1)—C(2)—C(7)—O(1) | 175.2(4) |

TABLE 4-continued

| Twist angle (°) of compound 4 | |
|---|---:|
| C(3)—C(2)—C(7)—O(1) | −5.8(7) |
| C(1)—C(2)—C(7)—C(8) | −4.5(6) |
| C(3)—C(2)—C(7)—C(8) | 174.5(4) |
| O(1)—C(7)—C(8)—C(9) | 97.5(5) |
| C(2)—C(7)—C(8)—C(9) | −82.8(5) |
| O(1)—C(7)—C(8)—C(13) | −82.0(5) |
| C(2)—C(7)—C(8)—C(13) | 97.7(5) |
| C(13)—C(8)—C(9)—C(10) | 0.7(6) |
| C(7)—C(8)—C(9)—C(10) | −178.8(4) |
| C(13)—C(8)—C(9)—Cl(1) | −179.8(3) |
| C(7)—C(8)—C(9)—Cl(1) | 0.7(6) |
| C(8)—C(9)—C(10)—C(11) | −1.8(7) |
| Cl(1)—C(9)—C(10)—C(11) | 178.7(3) |
| C(14)—O(2)—C(11)—C(12) | −9.1(7) |
| C(14)—O(2)—C(11)—C(10) | 170.4(4) |
| C(9)—C(10)—C(11)—C(12) | 1.2(7) |
| C(9)—C(10)—C(11)—O(2) | −178.4(4) |
| O(2)—C(11)—C(12)—C(13) | −179.9(4) |
| C(10)—C(11)—C(12)—C(13) | 0.6(7) |
| C(11)—C(12)—C(13)—C(8) | −1.7(7) |
| C(9)—C(8)—C(13)—C(12) | 1.1(6) |
| C(7)—C(8)—C(13)—C(12) | −179.4(4) |
| C(11)—O(2)—C(14)—C(15) | 89.6(5) |
| C(11)—O(2)—C(14)—C(19) | −94.7(6) |
| C(19)—C(14)—C(15)—C(16) | 2.4(7) |
| O(2)—C(14)—C(15)—C(16) | 178.0(4) |
| C(14)—C(15)—C(16)—C(17) | −1.5(7) |
| C(15)—C(16)—C(17)—C(18) | −0.6(8) |
| C(16)—C(17)—C(18)—C(19) | 1.9(8) |
| C(15)—C(14)—C(19)—C(18) | −1.1(8) |
| O(2)—C(14)—C(19)—C(18) | −176.7(5) |
| C(17)—C(18)—C(19)—C(14) | −1.1(8) |
| C(4)—N(4)—C(20)—C(21) | −157.1(4) |
| C(4)—N(4)—C(20)—C(24) | 80.3(5) |
| C(25)—O(4)—C(21)—C(20) | 155.1(5) |
| C(25)—O(4)—C(21)—C(22) | −85.8(5) |
| N(4)—C(20)—C(21)—O(4) | −54.8(4) |
| C(24)—C(20)—C(21)—O(4) | 68.4(4) |
| N(4)—C(20)—C(21)—C(22) | −175.8(3) |
| C(24)—C(20)—C(21)—C(22) | −52.6(4) |
| O(4)—C(21)—C(22)—C(23) | −65.9(5) |
| C(20)—C(21)—C(22)—C(23) | 51.9(5) |
| C(24)—O(3)—C(23)—C(22) | 59.8(5) |
| C(24)—O(3)—C(23)—C(26) | −178.1(4) |
| C(21)—C(22)—C(23)—O(3) | −55.0(5) |
| C(21)—C(22)—C(23)—C(26) | −173.8(4) |
| C(23)—O(3)—C(24)—C(20) | −61.6(4) |
| N(4)—C(20)—C(24)—O(3) | −179.7(3) |
| C(21)—C(20)—C(24)—O(3) | 58.1(5) |
| O(3)—C(23)—C(26)—O(5) | −61.2(5) |
| C(22)—C(23)—C(26)—O(5) | 59.8(6) |
| C(32)—N(5)—C(27)—C(28) | 1.5(5) |
| N(5)—C(27)—C(28)—C(29) | −0.3(5) |
| N(5)—C(27)—C(28)—C(33) | 177.2(4) |
| C(27)—C(28)—C(29)—C(32) | −1.0(5) |
| C(33)—C(28)—C(29)—C(32) | −178.4(4) |
| C(27)—C(28)—C(29)—C(30) | 178.8(5) |
| C(33)—C(28)—C(29)—C(30) | 1.4(8) |
| C(46)—N(8)—C(30)—N(6) | −3.0(6) |
| C(46)—N(8)—C(30)—C(29) | 176.6(4) |
| C(31)—N(6)—C(30)—N(8) | −176.9(4) |
| C(31)—N(6)—C(30)—C(29) | 3.5(6) |
| C(32)—C(29)—C(30)—N(8) | 174.5(4) |
| C(28)—C(29)—C(30)—N(8) | −5.2(8) |
| C(32)—C(29)—C(30)—N(6) | −5.8(6) |
| C(28)—C(29)—C(30)—N(6) | 174.4(5) |
| C(32)—N(7)—C(31)—N(6) | −3.2(7) |
| C(30)—N(6)—C(31)—N(7) | 1.4(8) |
| C(31)—N(7)—C(32)—N(5) | −177.5(4) |
| C(31)—N(7)—C(32)—C(29) | 0.3(6) |
| C(27)—N(5)—C(32)—N(7) | 175.9(4) |
| C(27)—N(5)—C(32)—C(29) | −2.2(5) |
| C(30)—C(29)—C(32)—N(7) | 4.1(6) |
| C(28)—C(29)—C(32)—N(7) | −176.1(4) |
| C(30)—C(29)—C(32)—N(5) | −177.9(4) |
| C(28)—C(29)—C(32)—N(5) | 1.9(5) |
| C(27)—C(28)—C(33)—O(6) | −165.9(5) |
| C(29)—C(28)—C(33)—O(6) | 11.0(8) |
| C(27)—C(28)—C(33)—C(34) | 11.2(7) |
| C(29)—C(28)—C(33)—C(34) | −171.8(4) |
| O(6)—C(33)—C(34)—C(39) | 63.5(8) |
| C(28)—C(33)—C(34)—C(39) | −113.7(7) |
| O(6)—C(33)—C(34)—C(35) | −111.6(6) |
| C(28)—C(33)—C(34)—C(35) | 71.1(6) |
| C(39)—C(34)—C(35)—C(36) | 1.2(9) |
| C(33)—C(34)—C(35)—C(36) | 176.3(5) |
| C(39)—C(34)—C(35)—Cl(2) | 175.0(6) |
| C(33)—C(34)—C(35)—Cl(2) | 0.1(7) |
| C(34)—C(35)—C(36)—C(37) | 0.9(9) |
| Cl(2)—C(35)—C(36)—C(37) | 177.1(5) |
| C(40)—O(7)—C(37)—C(38) | 74.0(15) |
| C(40)—O(7)—C(37)—C(36) | −110.9(10) |
| C(35)—C(36)—C(37)—O(7) | −177.1(7) |
| C(35)—C(36)—C(37)—C(38) | −2.1(12) |
| O(7)—C(37)—C(38)—C(39) | 176.3(9) |
| C(36)—C(37)—C(38)—C(39) | 1.3(15) |
| C(35)—C(34)—C(39)—C(38) | −2.1(12) |
| C(33)—C(34)—C(39)—C(38) | −177.5(8) |
| C(37)—C(38)—C(39)—C(34) | 0.9(16) |
| C(37)—O(7)—C(40)—C(41) | −159.7(11) |
| C(37)—O(7)—C(40)—C(45) | 17.5(17) |
| O(7)—C(40)—C(41)—C(42) | −176.2(8) |
| C(45)—C(40)—C(41)—C(42) | 6.5(13) |
| C(40)—C(41)—C(42)—C(43) | −1.0(11) |
| C(41)—C(42)—C(43)—C(44) | −3.6(11) |
| C(42)—C(43)—C(44)—C(45) | 2.9(13) |
| C(43)—C(44)—C(45)—C(40) | 2.4(15) |
| C(41)—C(40)—C(45)—C(44) | −7.3(15) |
| O(7)—C(40)—C(45)—C(44) | 175.6(10) |
| C(30)—N(8)—C(46)—C(50) | 76.0(5) |
| C(30)—N(8)—C(46)—C(47) | −165.5(4) |
| C(51)—O(9)—C(47)—C(46) | 162.8(5) |
| C(51)—O(9)—C(47)—C(48) | −77.6(6) |
| N(8)—C(46)—C(47)—O(9) | −54.8(4) |
| C(50)—C(46)—C(47)—O(9) | 65.5(4) |
| N(8)—C(46)—C(47)—C(48) | −175.9(4) |
| C(50)—C(46)—C(47)—C(48) | −55.6(5) |
| O(9)—C(47)—C(48)—C(49) | −63.1(5) |
| C(46)—C(47)—C(48)—C(49) | 54.2(5) |
| C(50)—O(8)—C(49)—C(52) | −177.3(4) |
| C(50)—O(8)—C(49)—C(48) | 59.4(5) |
| C(47)—C(48)—C(49)—O(8) | −54.7(5) |
| C(47)—C(48)—C(49)—C(52) | −174.3(4) |
| C(49)—O(8)—C(50)—C(46) | −62.6(5) |
| N(8)—C(46)—C(50)—O(8) | 177.7(3) |
| C(47)—C(46)—C(50)—O(8) | 59.7(5) |
| O(8)—C(49)—C(52)—O(10) | −65.2(5) |
| C(48)—C(49)—C(52)—O(10) | 56.3(5) |

TABLE 5

| Hydrogen bonds [Å and °] of compound 4 | | | | |
|---|---|---|---|---|
| D—H...A | d(D—H) | d(H...A) | d(D...A) | <(DHA) |
| O(5)—H(5A)...O(8)#1 | 0.84 | 2.01 | 2.829(5) | 165.3 |
| O(10)—H(10A)...O(3)#2 | 0.84 | 2.01 | 2.832(5) | 164.4 |
| N(1)—H(1A)...N(7) | 0.88 | 1.96 | 2.817(5) | 165.5 |
| N(4)—H(4A)...O(1) | 0.88 | 2.10 | 2.907(5) | 151.5 |
| N(5)—H(5B)...N(3) | 0.88 | 1.99 | 2.832(5) | 159.8 |
| N(8)—H(8A)...O(6) | 0.88 | 2.03 | 2.843(6) | 154.0 |

Symmetry transformation used to generate equivalent atoms: #1 x,y+1,z−1  #2 x,y−1,z+1

Example 5

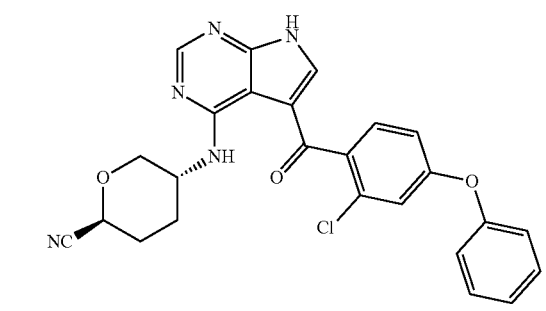

Route for Synthesis:

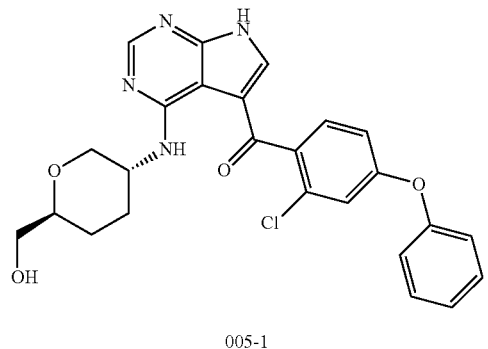

005-1

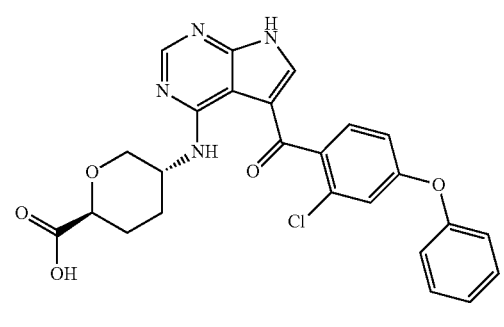

005-2

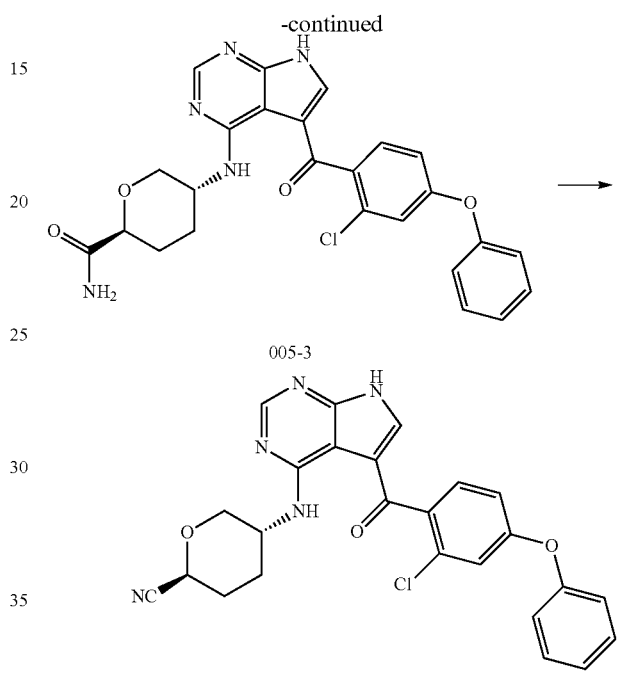

005-3

Compound 005-1 (i.e., reference example 1) was prepared according to the method described for Compound (I) in Patent WO2017111787.

Step 1: Synthesis of Compound 005-2

Compound 005-1 (0.4 g, 835.20 μmol, 1 eq) was dissolved in acetonitrile (5 mL), and iodobenzene diacetate (941.55 mg, 2.92 mmol, 3.5 eq) and 2,2,6,6-tetramethylpiperidine N-oxide (26.27 mg, 167.04 μmol, 0.2 eq) were added under nitrogen. Water (5 mL) was then added. After completion of the addition, the mixture was reacted at 30° C. for 12 h. The reaction solution was rotary evaporated to dryness to give compound 005-2, which was directly used in the next step without purification. LCMS: (ESI) m/z: 493.2 [M+H].

Step 2: Synthesis of Compound 005-3

Compound 005-2 (205.54 mg, 417 μmol, 1 eq) was dissolved in dichloromethane (5 mL). N,N'-carbonyl diimidazole (101.42 mg, 625.50 μmol, 1.5 eq) was added under nitrogen at 20° C. After stirring for 1 h, ammonia (146.14 mg, 4.17 mmol, 160.59 μL, 10 eq) was added dropwise to the reaction solution. After completion of the addition, the mixture was stirred vigorously for 0.5 h. The reaction solution was rotary evaporated to dryness to give compound 005-3, which was directly used in the next step without purification. LCMS: (ESI) m/z: 491.9 [M+H].

Step 3: Synthesis of Compound 5

Compound 005-3 (0.1 g, 203.28 μmol, 1 eq) was dissolved in N,N-dimethylformamide (1 mL), and cyanuric chloride (56.23 mg, 304.92 μmol, 1.5 eq) was added. After completion of the addition, the mixture was reacted at 20° C. for 1 h. The reaction solution was rotary evaporated to dryness to give a crude product. The crude product was purified by preparative separation (Column: Phenomenex Gemini-NX 80 mm*40 mm*3 μm; Mobile phase: [water (0.05% NH$_3$H$_2$O+10 mM NH$_4$HCO$_3$)-acetonitrile]; B (acetonitrile) %: 47%-77%, 8.5 min) to give compound 5. LCMS: (ESI) m/z: 473.9[M+H]. $^1$H NMR (400 MHz, CDCl$_3$) δ 9.32 (br d, J=7.4 Hz, 1H), 8.28 (s, 1H), 7.41-7.34 (m, 2H), 7.22-7.10 (m, 2H), 7.07-6.98 (m, 3H), 6.91 (br d, J=8.3 Hz, 1H), 4.71 (br s, 1H), 4.43 (br s, 1H), 4.15 (br d, J=11.8 Hz, 1H), 3.84 (br d, J=11.6 Hz, 1H), 2.36 (br d, J=13.9 Hz, 1H), 2.29-2.14 (m, 1H), 1.98 (br d, J=9.4 Hz, 1H), 1.93-1.73 (m, 1H).

Example 6

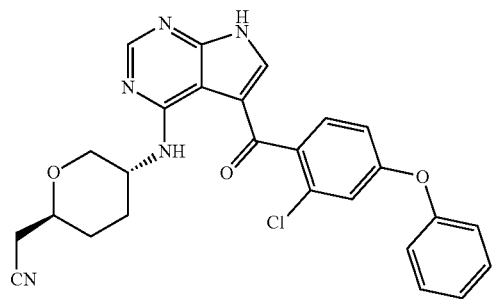

6

Route for Synthesis:

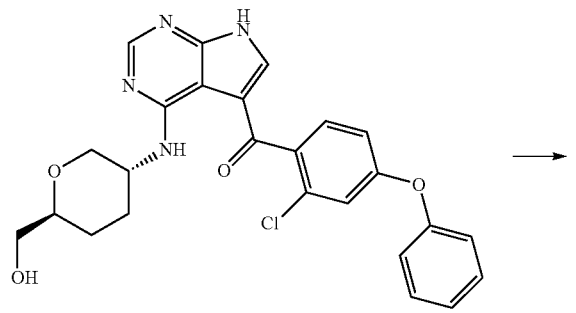

005-1

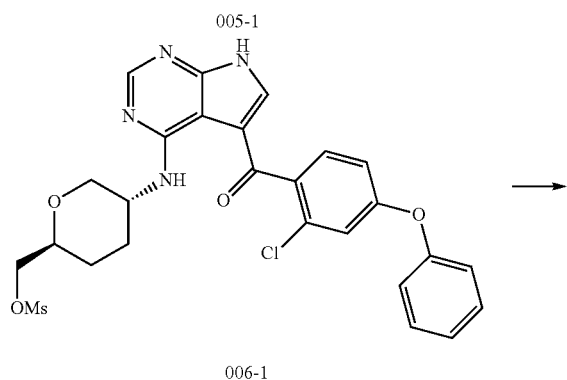

006-1

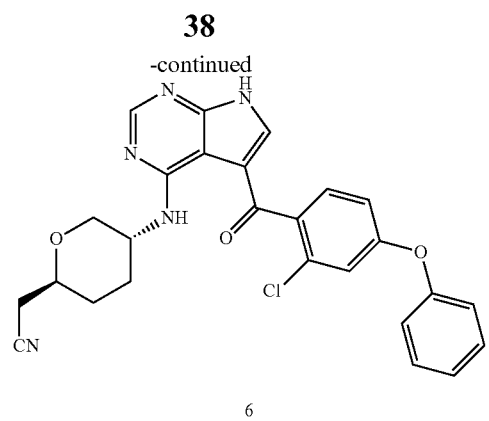

6

Step 1: Synthesis of Compound 006-1

Compound 005-1 (0.35 g, 730.80 μmol, 1 eq) was dissolved in dichloromethane (5 mL). Triethylamine (73.95 mg, 730.80 μmol, 1 eq) and methanesulfonyl chloride (117.20 mg, 1.02 mmol, 1.4 eq) were added at 0° C., and the mixture was reacted for 6 h. After completion of the reaction, water was added, and the mixture was extracted 3 times with 20 ml of dichloromethane each time. The organic phases were combined, dried over anhydrous sodium sulfate and rotary evaporated to dryness to remove the solvent. The crude product was purified by column chromatography (dichloromethane:methanol=50:1-20:1) to give compound 006-1. LCMS: (ESI) m/z: 557.0 [M+H].

Step 2: Synthesis of Compound 6

Compound 006-1 (100 mg, 179.53 μmol, 1 eq) was dissolved in N.N-dimethylformamide (2 mL), and sodium cyanide (130 mg, 2.65 mmol, 14.77 eq) was added. The mixture was reacted at 70° C. for 8 hr. After completion of the reaction, water was added. The mixture was extracted twice with 15 ml of ethyl acetate each time. The organic phases were combined, dried over anhydrous sodium sulfate, and rotary evaporated to dryness to remove the solvent. The crude product was purified by preparative separation (Column: Phenomenex Gemini-NX 80 mm*30 mm*3 μm; Mobile phase: [water (10 mM NH$_4$HCO$_3$)-acetonitrile]; B (acetonitrile) %: 44%-74%, 9.5 min) to give compound 6. LCMS: (ESI) m/z: 488.0 [M+H]. $^1$H NMR (CDCl$_3$, 400 MHz): δ 13.28 (br s, 1H), 8.79 (br d, J=7.5 Hz, 1H), 8.28 (s, 1H), 7.31-7.40 (m, 4H), 7.14-7.18 (m, 1H), 7.00-7.08 (m, 3H), 6.90 (dd, J=8.4, 2.1 Hz, 1H), 4.31 (br d, J=9.5 Hz, 2H), 3.55-3.65 (m, 1H), 3.20-3.29 (m, 1H), 2.53 (d, J=5.8 Hz, 2H), 2.29 (br s, 1H), 1.90 (br d, J=10.0 Hz, 1H), 1.60-1.72 ppm (m, 2H).

Example 7

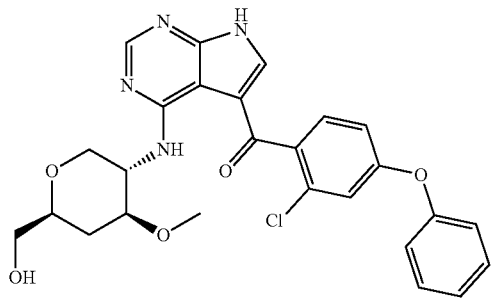

7

Route for Synthesis:

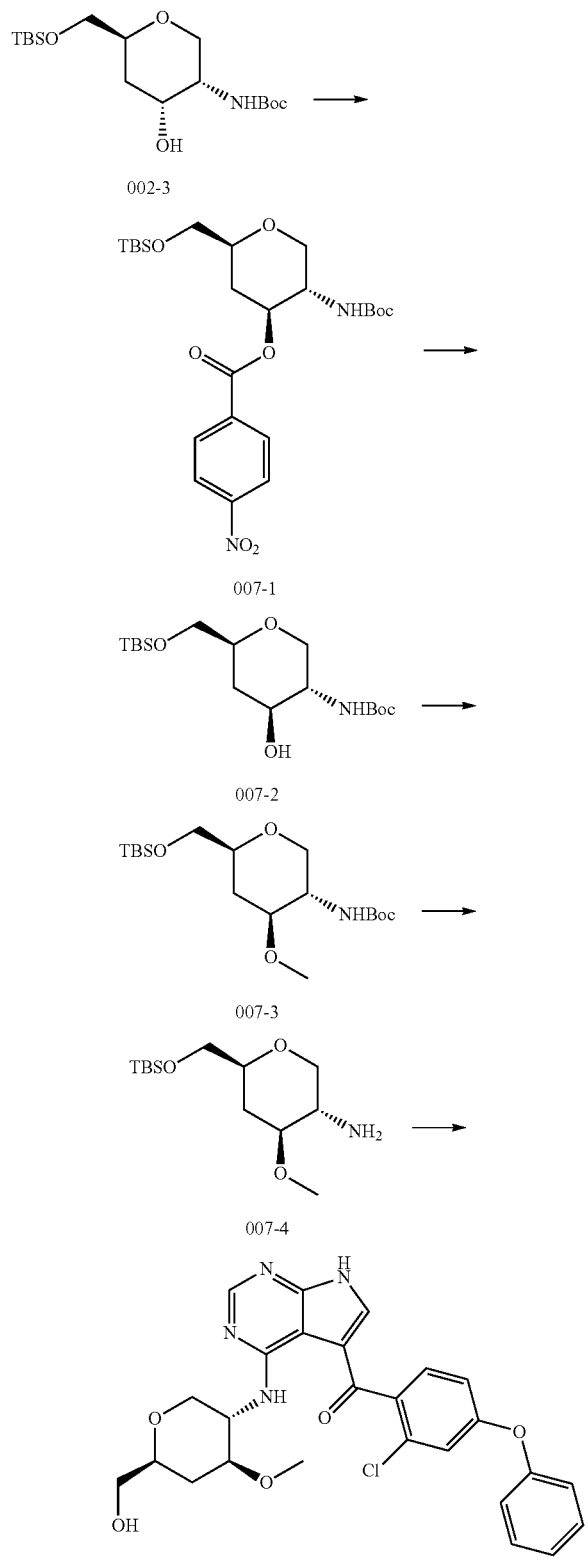

Step 1: Synthesis of Compound 007-1

Compound 002-3 (830 mg, 2.30 mmol, 1 eq), p-nitrobenzoic acid (613.84 mg, 3.67 mmol, 1.6 eq) and triphenylphosphine (2.41 g, 9.18 mmol, 4 eq) were dissolved in toluene (14 mL), and diethyl azodicarboxylate (1.60 g, 9.18 mmol, 1.67 mL, 4 eq) was then added. The mixture was reacted at 65° C. for 12 hours. After completion of the reaction, water was added. The mixture was extracted 3 times with 20 ml of ethyl acetate each time. The organic phases were combined, dried over anhydrous sodium sulfate and rotary evaporated to dryness to remove the solvent. The crude product was purified by column chromatography (petroleum ether:ethyl acetate=50:1-20:1) to give compound 007-1.

Step 2: Synthesis of Compound 007-2

Compound 007-1 (650 mg, 1.27 mmol, 1 eq) and potassium carbonate (439.81 mg, 3.18 mmol, 2.5 eq) were dissolved in anhydrous tetrahydrofuran (5 mL) and methanol (5 mL). The mixture was reacted at 20° C. for 12 h. After completion of the reaction, the mixture was filtered, and rotary evaporated to dryness to remove the solvent. The crude product was purified by column chromatography (petroleum ether:ethyl acetate=50:1-10:1) to give compound 007-2. LCMS: (ESI) m/z: 306.1 [M-$^t$Bu+H].

Step 3: Synthesis of Compound 007-3

Compound 007-2 (340 mg, 940.40 μmol, 1 eq) was dissolved in acetonitrile (5 mL). Silver oxide (653.79 mg, 2.82 mmol, 3 eq) and iodomethane (1.33 g, 9.40 mmol, 10 eq) were then added under nitrogen. The mixture was reacted at 80° C. in a sealed tube for 40 hours. After completion of the reaction, the mixture was filtered and rotary evaporated to dryness. The crude product was purified by column chromatography (petroleum ether:ethyl acetate=50:1-20:1) to give compound 007-3.

Step 4: Synthesis of Compound 007-4

Compound 007-3 (240 mg, 639.02 μmol, 1 eq) was dissolved in 1,4-dioxane (4 mL), and HCl/dioxane (4 M, 4.79 mL, 30 eq) was then added. The mixture was reacted at 20° C. for 3 h. After completion of the reaction, the mixture was directly rotary evaporated to dryness to give 007-4 and the crude product was directly used in the next step. LCMS: (ESI) m/z: 161.8 [M+H].

Step 4: Synthesis of Compound 7

Compound 007-4 (100 mg, 620.35 μmol, 1 eq) and intermediate A (143.01 mg, 372.21 μmol, 0.6 eq) were dissolved in isopropanol (2 mL), and N,N-diisopropylethylamine (240.52 mg, 1.86 mmol, 3 eq) was then added. The mixture was reacted with microwave at 130° C. for 1 h. The solvent was rotary evaporated to dryness and the crude product was purified by preparative separation (Column: Phenomenex Gemini-NX 75 mm*30 mm*3 μm; Mobile phase: [water (0.225% formic acid)-acetonitrile]; B (acetonitrile) %: 35%-55%, 7 min) to give compound 7. LCMS: (ESI) m/z: 509.1 [M+H]. $^1$H NMR (CDCl3, 400 MHz): δ=9.10 (br d, J=7.0 Hz, 1H), 8.34 (s, 1H), 7.37-7.49 (m, 4H), 7.21-7.28 (m, 1H), 7.07-7.16 (m, 3H), 6.99 (dd, J=8.3, 2.3 Hz, 1H), 4.30-4.52 (m, 2H), 3.55-3.85 (m, 4H), 3.50 (s, 3H), 3.31 (br t, J=10.8 Hz, 1H), 2.22 (br dd, J=12.7, 3.6 Hz, 1H), 1.54 ppm (q, J=11.5 Hz, 1H).

Example 8

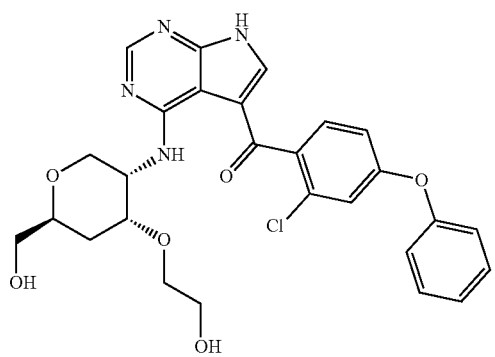

Route for Synthesis:

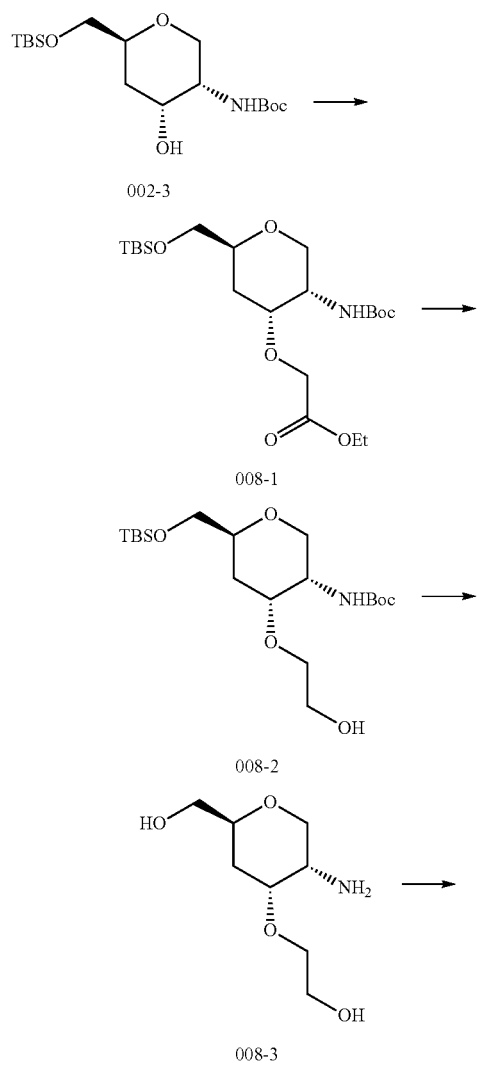

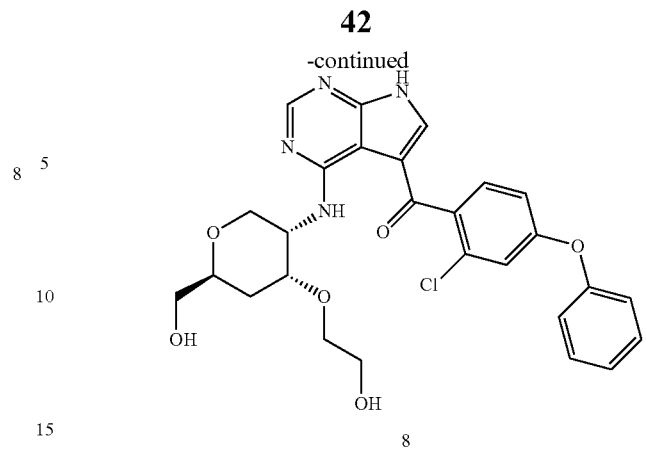

Step 1: Synthesis of Compound 008-1

Compound 002-3 (1 g, 2.77 mmol, 1 eq) was dissolved in 1,2-dichloroethane (10 mL), and rhodium (II) acetate dimer (12.22 mg, 27.66 μmol, 0.01 eq) was then added. Ethyl diazoacetate (315.59 mg, 2.77 mmol, 1 eq) was added dropwise at 80° C., and the mixture was reacted for 8 h. After completion of the reaction, water was added, and the mixture was extracted three times with 30 mL of ethyl acetate each time. The organic phases were combined and dried over anhydrous sodium sulfate. The solvent was rotary evaporated to dryness and the crude product was purified by column chromatography (petroleum ether:ethyl acetate=50: 1-20:1) to give compound 008-1. LCMS: (ESI) m/z: 348.2 [M-$^t$Bu+H].

Step 2: Synthesis of Compound 008-2

Compound 008-1 (1.6 g, 3.57 mmol, 1 eq) was dissolved in anhydrous ethanol (15 mL), and sodium borohydride (405.68 mg, 10.72 mmol, 3 eq) was added in an ice bath. The mixture was slowly warmed to room temperature and reacted for 12 h. After completion of the reaction, 30 mL of saturated ammonium chloride was added and the mixture was extracted 3 times with 30 mL of ethyl acetate each time. The organic phases were combined and dried over anhydrous sodium sulfate. The solvent was rotary evaporated to dryness and the crude product was purified by column chromatography (petroleum ether:ethyl acetate=40:1-15:1) to give compound 008-2. LCMS: (ESI) m/z: 306.2 [M-Boc+H].

Step 3: Synthesis of Compound 008-3

Compound 008-2 (330.00 mg, 813.61 μmol, 1 eq) was dissolved in 1,4-dioxane (4 mL), and HCl/dioxane (4 M, 6.10 mL, 30 eq) was then added. The mixture was reacted at 20° C. for 12 h. Solid precipitated. The mixture was filtered to give product 008-3. LCMS: (ESI) m/z: 190.2 [M+H].

Step 4: Synthesis of Compound 8

Compound 008-3 (40 mg, 175.68 μmol, 1 eq) and intermediate A (67.50 mg, 175.68 μmol, 1 eq) were dissolved in isopropanol (1.5 mL), and diisopropylethylamine (68.12 mg, 527.04 μmol, 3 eq) was added. The mixture was reacted with microwave at 130° C. for 1 h. The solvent was rotary evaporated to dryness and the crude product was purified by preparative separation (Column: Phenomenex Gemini-NX 75 mm*30 mm*3 μm; Mobile phase: [water (0.225% formic acid)-acetonitrile]; B (acetonitrile) %: 30%-50%, 7 min) to give compound 8. LCMS: (ESI) m/z: 539.1 [M+H]. $^1$H NMR (CDCl$_3$, 400 MHz): δ=9.46 (d, J=8.3 Hz, 1H), 8.33 (s, 1H), 7.41-7.48 (m, 4H), 7.23-7.28 (m, 1H), 7.13 (d, J=7.8 Hz, 2H), 7.08 (d, J=2.3 Hz, 1H), 6.96 (dd, J=8.5, 2.3 Hz, 1H), 4.54-4.67 (m, 1H), 3.96-4.14 (m, 3H), 3.83-3.92 (m, 2H), 3.69-3.82 (m, 3H), 3.49-3.64 (m, 2H), 2.09 (br d, J=14.6 Hz, 1H), 1.71 ppm (br t, J=12.2 Hz, 1H)

Example 9

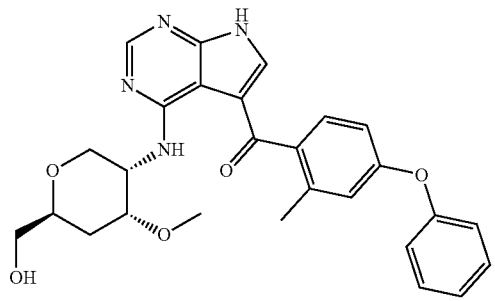

Route for Synthesis:

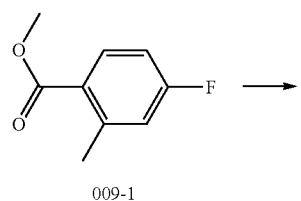

009-1

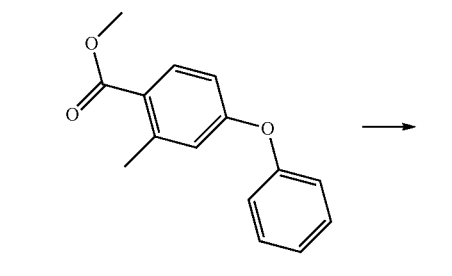

009-2

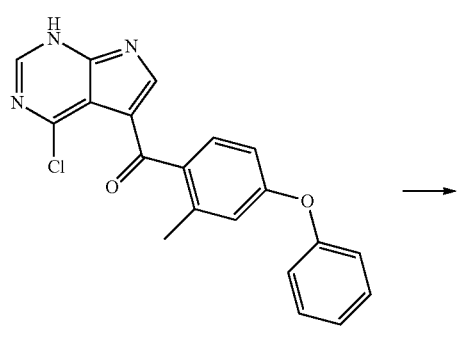

009-3

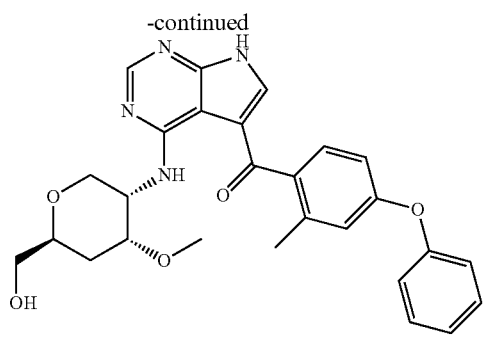

9

Step 1: Synthesis of Compound 009-2

Compound 009-1 (4.5 g, 26.76 mmol, 1 eq) and phenol (2.52 g, 26.76 mmol, 1 eq) were added to N,N-dimethylformamide (50 mL), and cesium carbonate (8.72 g, 26.76 mmol, 1 eq) was added. The mixture was reacted at 120° C. for 5 h. The reaction solution was filtered, and water was added. The mixture was extracted three times with 50 mL of ethyl acetate each time. The organic phases were combined and rotary evaporated to dryness to give a crude product. The crude product was purified by column chromatography (petroleum ether:ethyl acetate=50:1) to give compound 009-2. LCMS: (ESI) m/z: 242.80 [M+H].

Step 2: Synthesis of Compound 009-3

Compound B (913.84 mg, 3.93 mmol, 1 eq) was added in tetrahydrofuran (10 mL), and n-butyllithium (2.5 M, 3.30 mL, 2.1 eq) was added at −78° C. The mixture was reacted for 1.5 h. A solution of compound 009-2 (1 g, 4.13 mmol, 1.05 eq) in tetrahydrofuran (5 mL) was then added dropwise. After completion of the addition, the mixture was reacted with stirring for 6 hours. The reaction was quenched with 2 mL of water. The organic phase was separated, and the aqueous phase was extracted twice with 30 mL ethyl acetate each time. The organic phases were combined, dried over anhydrous sodium sulfate, and filtered. The filtrate was rotary evaporated to dryness to give a crude product. The crude product was purified by column chromatography (dichloromethane:methanol=10:1) to give compound 009-3. LCMS: (ESI) m/z: 387.20 [M+Na].

Step 3: Synthesis of Compound 9

Compound 004-2 (159.52 mg, 989.57 μmol, 1.2 eq) and compound 009-3 (0.3 g, 824.64 μmol, 1 eq) were dissolved in isopropanol (5 mL), and N,N-diisopropylethylamine (266.44 mg, 2.06 mmol, 2.5 eq) was added. The mixture was reacted with microwave at 130° C. for 2 h. The crude product was purified by preparative separation (Column: Phenomenex Gemini-NX 150 mm*40 mm*5 μm; Mobile phase: [water (0.225% formic acid)-acetonitrile]; B (acetonitrile) %: 37%-57%, 8 min) to give compound 9. LCMS: (ESI) m/z: 489.15 [M+H]. $^1$H NMR (400 MHz, CDCl$_3$) δ=9.37 (d, J=8.3 Hz, 1H), 8.25-8.15 (m, 1H), 7.39-7.26 (m, 4H), 7.14-7.06 (m, 1H), 7.00 (dd, J=1.0, 8.5 Hz, 2H), 6.87-6.74 (m, 2H), 4.54-4.38 (m, 1H), 3.98 (dd, J=5.3, 10.5 Hz, 1H), 3.85-3.73 (m, 2H), 3.71-3.62 (m, 2H), 3.54-3.44 (m, 4H), 2.30 (s, 3H), 2.01-1.89 (m, 1H), 1.69-1.56 (m, 1H).

Example 10

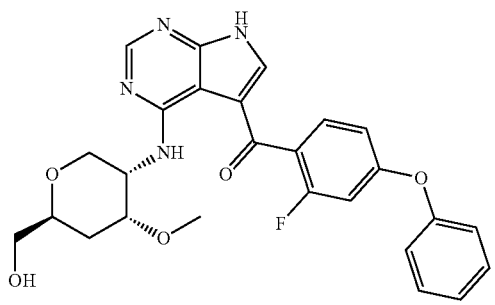

Route for Synthesis:

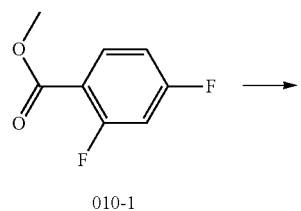

010-1

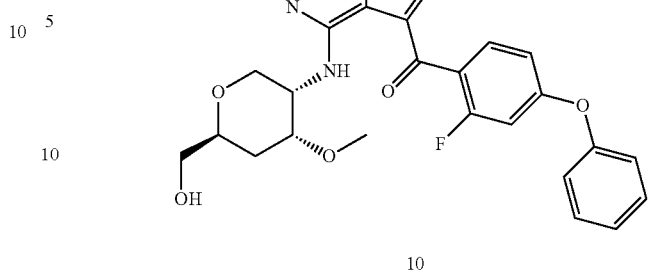

010-2

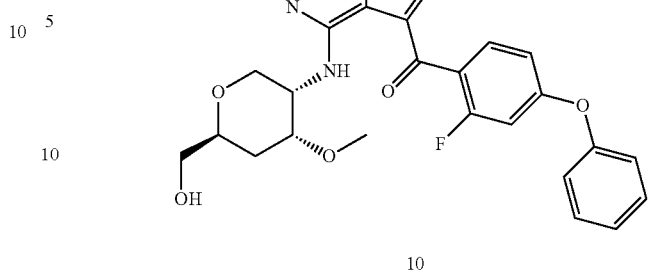

010-3

-continued

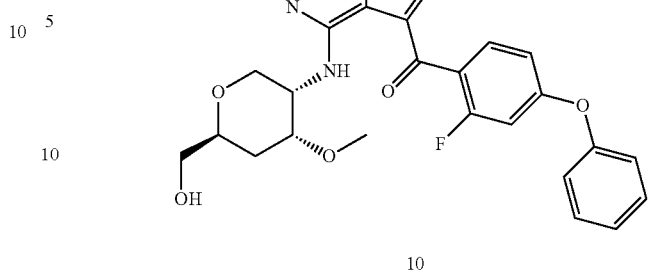

10

Step 1: Synthesis of Compound 010-2

Compound 010-1 (5 g, 29.05 mmol, 1 eq) and phenol (2.73 g, 29.05 mmol, 1 eq) were dissolved in N,N-dimethylformamide (50 mL), and cesium carbonate (9.46 g, 29.05 mmol, 1 eq) was added. The mixture was reacted at 85° C. for 12 h. The reaction solution was filtered, and water was added. The mixture was extracted three times with 50 mL ethyl acetate each time. The organic phases were combined and rotary evaporated to dryness to give a crude product. The crude product was purified by preparative separation (Column: Welch Xtimate C18 100*40 mm*3 μm; Mobile phase: [water (0.075% formic acid)-acetonitrile]; acetonitrile %: 40%-70%, 8 min) to give compound 010-2. LCMS: (ESI) m/z: 246.80 [M+H]. $^1$H NMR (400 MHz, CDCl$_3$) δ=7.84 (t, J=8.6 Hz, 1H), 7.38-7.27 (m, 2H), 7.22-7.10 (m, 1H), 7.05-6.95 (m, 2H), 6.70 (dd, J=2.3, 8.8 Hz, 1H), 6.59 (dd, J=2.4, 12.1 Hz, 1H), 3.88-3.81 (m, 3H).

Step 2: Synthesis of Compound 010-3

Compound B (858.26 mg, 3.69 mmol, 1 eq) was added to tetrahydrofuran (10 mL), and n-butyllithium (2.5 M, 3.10 mL, 2.1 eq) was added at −78° C. The mixture was reacted for 1.5 h. A solution of compound 010-2 (1 g, 4.06 mmol, 1.1 eq) in tetrahydrofuran (10 mL) was then added dropwise at −78° C. After completion of the addition, the mixture was reacted with stirring for 6 h. The reaction was quenched with 2 mL of water. The organic phase was separated, and the aqueous phase was extracted twice with 30 mL ethyl acetate each time. The organic phases were combined, and dried over anhydrous sodium sulfate. The mixture was filtered, and the filtrate was rotary evaporated to dryness to give a crude product. The crude product was purified by column chromatography (dichloromethane:methanol=10:1) to give compound 010-3. LCMS: (ESI) m/z: 367.80 [M+H].

Step 3: Synthesis of Compound 10

Compound 004-2 (146.11 mg, 906.39 μmol, 1 eq) and compound 010-3 (0.3 g, 815.75 μmol, 0.9 eq) were dissolved in isopropanol (5 mL), and N,N-diisopropylethylamine (292.85 mg, 2.27 mmol, 2.5 eq) was added. The mixture was reacted with microwave at 130° C. for 2 h. The crude product was purified by preparative separation (Column: Phenomenex Gemini-NX 150 mm*40 mm*5 μm; Mobile phase: [water (0.225% formic acid)-acetonitrile]; B (acetonitrile) %: 37%-57%, 8 min) to give compound 10. LCMS: (ESI) m/z: 493.20 [M+H]. $^1$H NMR (400 MHz, CDCl$_3$) δ=9.20 (d, J=8.3 Hz, 1H), 8.35 (s, 1H), 7.62-7.42 (m, 4H), 7.28-7.23 (m, 1H), 7.14 (d, J=7.5 Hz, 2H), 6.88 (dd, J=2.3, 8.5 Hz, 1H), 6.78 (dd, J=2.3, 11.0 Hz, 1H), 4.62-4.49 (m, 1H), 4.06 (dd, J=5.1, 10.9 Hz, 1H), 3.85 (br s, 2H), 3.81-3.71 (m, 2H), 3.64-3.52 (m, 4H), 2.03 (br d, J=13.8 Hz, 1H), 1.70 (br s, 1H).

Example 11

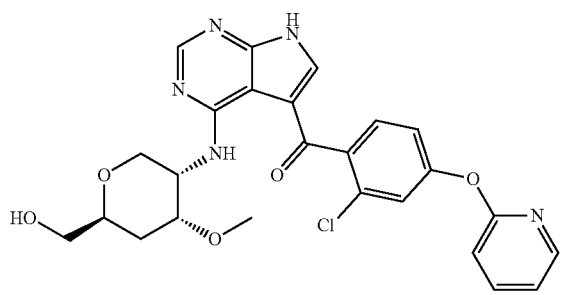

11

Route for Synthesis:

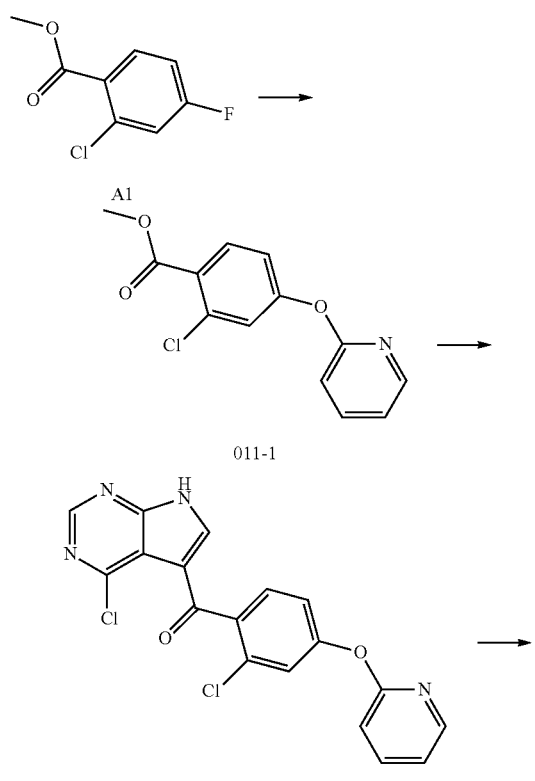

Step 1: Synthesis of Compound 011-1

Compound A1 (4 g, 21.21 mmol, 1 eq) and 2-hydroxypyridine (2.02 g, 21.21 mmol, 1 eq) were dissolved in N,N-dimethylformamide (15 mL), and potassium carbonate (3.52 g, 25.45 mmol, 1.2 eq) was then added. The mixture was reacted at 70° C. for 16 h. 25 mL of water was added, and the mixture was extracted twice with 50 mL ethyl acetate each time. The organic phases were combined, washed once with 20 ml of saturated sodium chloride solution and dried over anhydrous sodium sulfate. The solvent was rotary evaporated to dryness. Then the residue was slurried with 15 mL of ethyl acetate at room temperature and filtered to give compound 011-1. LCMS: (ESI) m/z: 263.9 [M+H]. $^1$H NMR (400 MHz, CDCl$_3$-d) δ=7.99 (d, J=8.0 Hz, 1H), 7.57 (d, 1H), 7.48-7.40 (m, 2H), 7.32 (d, 1H), 6.69 (d, 1H), 6.30 (t, 1H), 4.06-3.92 (m, 3H).

Step 2: Synthesis of Compound 011-2

Compound B (839.65 mg, 3.61 mmol, 1 eq) was dissolved in tetrahydrofuran (10 mL). The mixture was cooled to −78° C. under nitrogen, and n-butyllithium (2.5 M, 2.89 mL, 2 eq) was then added dropwise. The mixture was reacted for 1.5 h. Compound 011-1 (1.00 g, 3.79 mmol, 1.05 eq) was then added, and the mixture was reacted for 3 h. The reaction was quenched by adding 15 mL of water, and the mixture was extracted twice with 30 mL of ethyl acetate each time. The organic phases were combined, dried over anhydrous sodium sulfate, and rotary evaporated to dryness to remove the solvent. The residue was purified by column chromatography (dichloromethane:methanol=20:1-10:1) to give compound 011-2. LCMS: (ESI) m/z: 385.0 [M+H].

Step 3: Synthesis of Compound 11

Compound 004-2 (35.15 mg, 218.07 mmol, 1.2 eq) and compound 011-2 (70 mg, 181.72 μmol, 1 eq) were added to isopropanol (3 mL), and N,N-diisopropylethylamine (58.72 mg, 454.31 μmol, 2.5 eq) was then added. The mixture was reacted with microwave at 125° C. for 1.5 h, and then evaporated under reduced pressure to remove the solvent. The crude product was purified by preparative separation (Column: Phenomenex Gemini-NX 75 mm*30 mm*5 μm; Mobile phase: [water (0.225% formic acid)-acetonitrile]; B (acetonitrile) %: 15%-35%, 7 min) to give compound 11. LCMS: (ESI) m/z: 510.1 [M+H]. $^1$H NMR (400 MHz, CD$_3$OD) δ=9.26 (d, J=8.0 Hz, 1H), 8.25 (s, 1H), 7.76-7.66 (m, 4H), 7.60 (s, 1H), 7.53 (d, 1H), 6.71 (d, 1H), 6.57 (t, 1H), 4.49 (s, 1H), 4.02 (m, 1H), 3.89-3.75 (m, 2H), 3.68 (t, 1H), 2.16 (d, 1H), 1.67-1.54 (m, 1H).

Example 12

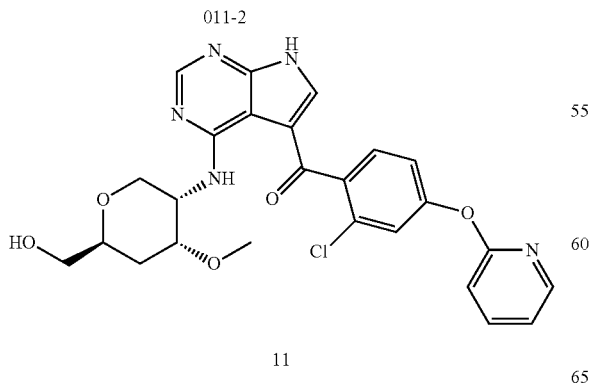

11

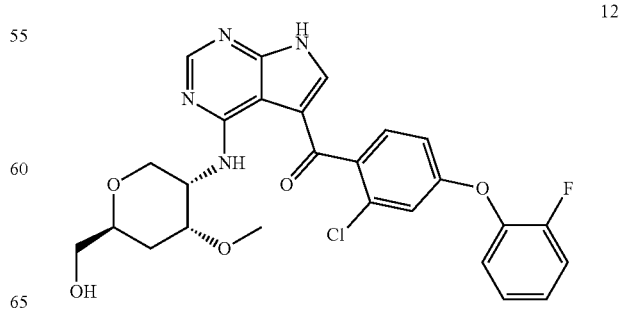

12

Route for Synthesis:

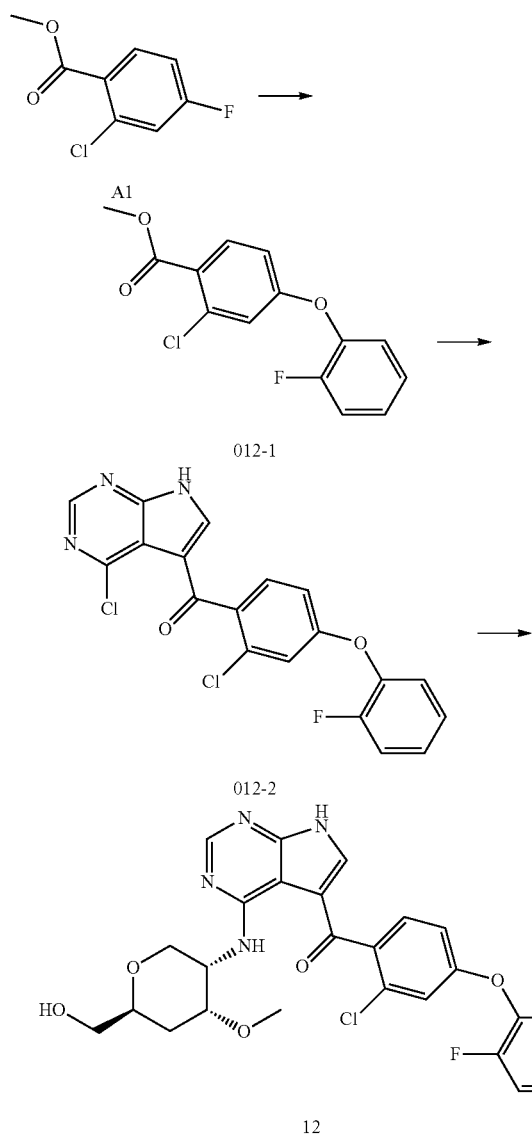

Step 1: Synthesis of Compound 012-1

Compound A1 (5 g, 26.51 mmol, 1 eq) and 2-fluorophenol (3.57 g, 31.82 mmol, 1.2 eq) were dissolved in N,N-dimethylformamide (25 mL), and cesium carbonate (10.37 g, 31.82 mmol, 1.2 eq) was then added. The mixture was reacted at 70° C. for 3 h. 25 mL of water was added, and the mixture was extracted twice with 50 mL of ethyl acetate each time. The organic phases were combined, and dried over anhydrous sodium sulfate. The solvent was rotary evaporated to dryness, and the residue was purified by silica gel column chromatography (petroleum ether:ethyl acetate=50:1-30:1) to give compound 012-1. LCMS: (ESI) m/z: 280.9 [M+H].

Step 2: Synthesis of Compound 012-2

Compound B (720 mg, 3.10 mmol, 1 eq) was dissolved in tetrahydrofuran (6 mL). The mixture was cooled to −78° C. under nitrogen, and n-butyllithium (2.5 M, 2.60 mL, 2.1 eq) was then added dropwise. After the mixture was reacted for 1 h, a solution of compound 012-1 (724.44 mg, 2.58 mmol, 1 eq) in tetrahydrofuran (4 mL) was added, and the mixture was reacted for another 4 h. The reaction was quenched by adding 15 mL of water. The mixture was extracted twice with 30 mL of ethyl acetate each time. The organic phases were combined, dried over anhydrous sodium sulfate, and rotary evaporated to dryness to remove the solvent. The residue was purified by column chromatography (dichloromethane:methanol=50:1-30:1) to give compound 012-2. LCMS: (ESI) m/z: 402.0 [M+H].

Step 3: Synthesis of Compound 12

Compound 004-2 (60 mg, 372.21 μmol, 1 eq) and compound 012-2 (119.76 mg, 297.77 μmol, 0.8 eq) were added to isopropanol (2 mL), and N,N-diisopropylethylamine (144.31 mg, 1.12 mmol, 3 eq) was then added. The mixture was reacted with microwave at 130° C. for 1.5 h, and evaporated under reduced pressure to remove the solvent. The crude product was purified by preparative separation (Column Phenomenex Gemini-NX 75 mm*30 mm*5 μm; Mobile phase: [water (0.225% formic acid)-acetonitrile]; B (acetonitrile) %: 35%-65%, 7 min) to give compound 12. LCMS: (ESI) m/z: 527.1 [M+H]. $^1$H NMR (CDCl$_3$, 400 MHz): δ=12.60-13.25 (m, 1H), 9.28 (br d, J=7.3 Hz, 1H), 8.33 (s, 1H), 7.43 (br d, J=8.3 Hz, 1H), 7.32-7.39 (m, 1H), 7.16-7.27 (m, 4H), 7.07 (s, 1H), 6.96 (br d, J=8.0 Hz, 1H), 4.56 (br s, 1H), 4.07 (br d, J=5.0 Hz, 1H), 3.84 (br s, 2H), 3.74 (br d, J=15.3 Hz, 2H), 3.58 (s, 4H), 2.03 (br d, J=12.0 Hz, 1H), 1.62-1.75 ppm (m, 1H).

Example 13

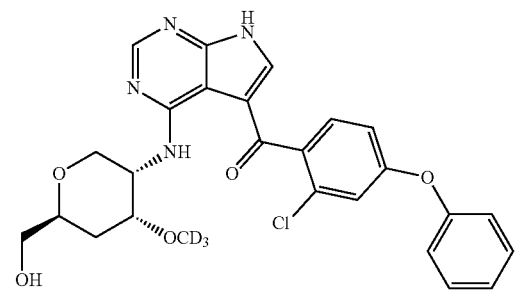

Route for Synthesis:

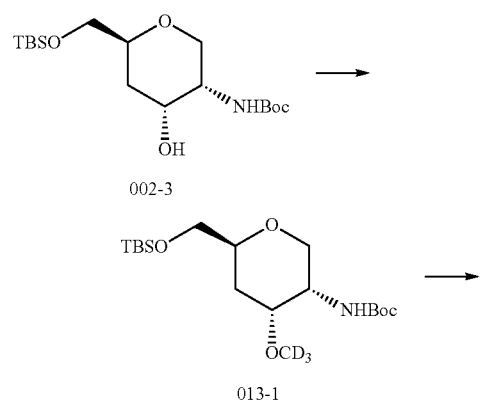

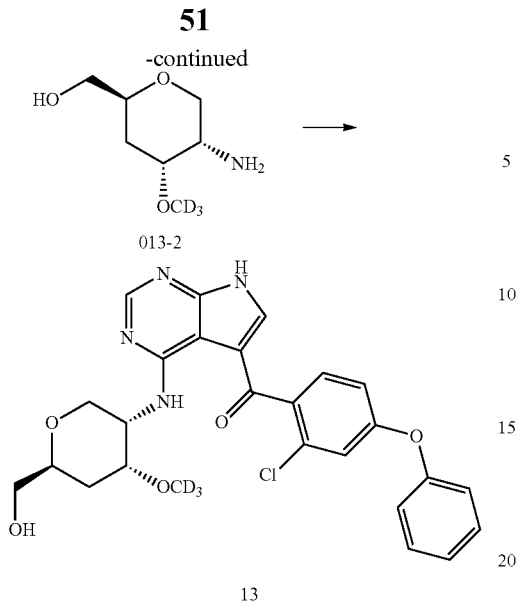

Step 1: Synthesis of Compound 013-1

Compound 002-3 (500 mg, 1.38 mmol, 1 eq) was dissolved in acetonitrile (5 mL). Silver oxide (961.45 mg, 4.15 mmol, 3 eq) and deuterated iodomethane (2.00 g, 13.83 mmol, 10 eq) were then added under nitrogen. The mixture was reacted at 80° C. in a sealed tube for 48 hours. After completion of the reaction, the mixture was filtered and rotary evaporated to dryness. The crude product was purified by column chromatography (petroleum ether:ethyl acetate=50:1-20:1) to give compound 013-1. LCMS: (ESI) m/z: 279.1 [M+H].

Step 2: Synthesis of Compound 013-2

Compound 013-1 (140 mg, 369.79 μmol, 1 eq) was dissolved in 1,4-dioxane (2 mL), and hydrochloric acid/1,4-dioxane (4 M, 2.77 mL, 30 eq) was then added. The mixture was reacted at 20° C. for 3 h. After completion of the reaction, the mixture was directly rotary evaporated to dryness to give 013-2 and the crude product was directly used in the next step.

Step 3: Synthesis of Compound 13

Compound 013-2 (60 mg, 365.37 μmol, 1 eq) and intermediate A (140.38 mg, 365.37 μmol, 1 eq) were dissolved in isopropanol (1 mL), and diisopropylethylamine (141.66 mg, 1.10 mmol, 190.92 μL, 3 eq) was then added. The mixture was reacted with microwave at 130° C. for 4 h. The solvent was rotary evaporated to dryness and the crude product was purified by preparative separation (Column: Phenomenex Gemini-NX 75 mm*30 mm*3 μm; Mobile phase: [water (0.225% formic acid)-acetonitrile]; B (acetonitrile) %: 35%-55%, 7 min) to give compound 13. LCMS: (ESI) m/z: 512.1 [M+H]. $^1$H NMR (CDCl$_3$, 400 MHz): δ=9.30 (br d, J=7.3 Hz, 1H), 8.32 (br s, 1H), 7.35-7.49 (m, 4H), 7.25 (br d, J=7.5 Hz, 1H), 7.11 (br d, J=8.0 Hz, 3H), 6.98 (br d, J=7.5 Hz, 1H), 4.56 (br s, 1H), 4.07 (br s, 1H), 3.69-3.94 (m, 4H), 3.59 (br d, J=6.5 Hz, 1H), 2.02 (br d, J=13.6 Hz, 1H), 1.70 ppm (br t, J=12.3 Hz, 1H).

Biological Assay Data:

Assay Example 1: BTK Enzyme Activity Assay

The specific assay process of BTK enzyme activity assay is as follows: Buffer: 20 mM 2-[4-(2-hydroxyethyl)-1-piperazinyl]ethanesulfonic acid (Hepes) (pH 7.5), 10 mM magnesium chloride, 1 mM ethylenebis(oxyethylenenitrilo)tetraacetic acid (EGTA), 0.02% polyoxyethylene dodecyl ether (Brij35), 0.02 mg/mL BSA, 0.1 mM sodium vanadate (Na$_3$VO$_4$), 2 mM dithiothreitol (DTT), 1% DMSO, 200 μM adenosine triphosphate (ATP).

1. The substrate was prepared in freshly prepared reaction buffer;
2. The required cofactor was added to the above-mentioned substrate solution;
3. The kinase BTK$^{C481S}$ was added to the above-mentioned substrate solution and mixed well;
4. The compound dissolved in DMSO was added to the kinase reaction mixture by Echo550 (Acoustic technology; nanoliter range), and the mixture was incubated at room temperature for 20 minutes;
5. $^{33}$P-ATP (specific radioactivity of 10 μCi/μL) was added to the reaction mixture to initiate the reaction;
6. The mixture was incubated at room temperature for 2 hours;
7. The radioactivity was detected by filter-binding method;
8. Kinase activity data represented the percentage of remaining kinase activity in the assay sample compared to the vehicle (dimethyl sulfoxide) reaction. IC$_{50}$ values and fitted curve were obtained using Prism (GraphPad software), and the results were shown in Table 6.

TABLE 6

Results of BTK activity assay in vitro

| Compound No. | BTK$^{C481S}$ IC$_{50}$(nM) |
|---|---|
| 1 | 1.7 |
| 2 | 12.5 |
| 3 | 6.7 |
| 4 | 7.3 |
| 5 | 10.7 |
| 6 | 6.5 |
| 7 | 43.6 |
| 8 | 8.9 |
| 9 | 15.2 |
| 10 | 14.9 |
| 12 | 39.8 |
| 13 | 15.1 |

Conclusion: The compounds of the present disclosure have strong inhibitory effect on BTK$^{C481S}$ mutation.

Assay Example 2: BTK Cell Activity Assay

1. Cell Culture and Passage

The medium, trypsin and 1×PBS used in the cell passage process were preheated in a 37° C. water bath. The supernatant was aspirated.

1 mL of trypsin was added to rinse, and the rinse solution was aspirated. 1 mL of trypsin was added, respectively, and cells were digested at 37° C. until the cells fell off. 10 mL of culture medium was added and mixed well. The mixture was centrifuged at 1000 rpm for 5 min and the cells were resuspended in 10 mL of culture medium. 0.7 mL of cell suspension was pipetted into a counting cup and counted on ViCell XR to respectively obtain a cell density of 0.327 million/mL. 1.17 mL of cell suspension and culture medium were weighed, respectively, to dilute the cell suspension. According to the microplate layout diagram below, 100 μL of phosphate buffer was added to the peripheral wells of the 384-well microplate, and 40 μL of cell suspension was added to other wells, respectively. The cell plate was then cultured in an incubator.

2. Dosing (1) Preparation of compound:

A 9 μL dilution of the compound to be assayed was added to a shallow-well plate for Pod (Labcyte, #LP-0200). The shallow-well plate was centrifuged at 2500 rpm for 30 s.

(2) The cell plate was removed from the incubator.

(3) According to the microplate layout diagram below, compounds were serially diluted 3-fold in Pod to obtain 10 concentrations. The diluted compounds were added to the cell plate at 100 nL, respectively, and then the cell plate was returned to the incubator for culture.

3. At Day 0, 20 μL of CellTiter Glo was added to the plate with DMSO added, and the mixture was shaken in the dark for 10 minutes. The plate was read with Envision.

4. At Day 5: CTG was added and the plate was read.

(1) After being cultured for 72 h, 20 μL of Cell Titer Glo was added to the cell plate, and the mixture was shaken in the dark for 10 minutes.

(2) The plate was read with Envision.

Assay Results

1. Average value and standard deviation of 0% inhibition (DMSO well, MAX) and 100% inhibition (day 0, DMSO) in each group were calculated;
2. Inhibition rate (%)=(1−(sample value−average value of 100% inhibition)/(average value of 0% inhibition−average value of 100% inhibition))*100;
3. Curve was fitted by GraphPad 5.0 software, and the results were shown in Table 7.

TABLE 7

Results of BTK activity assay in vitro

| Compound No. | Relative $IC_{50}$ (nM) |
|---|---|
| 2 | 269.0 |
| 3 | 217.2 |
| 4 | 260.9 |

Conclusion: The compounds of the present disclosure have good inhibitory effect on TMD8 cells.

Assay Example 3: Assay of Kinetic Solubility

The assay compound was dissolved in DMSO to prepare 10 mmol/L stock solution. 980 μL of dissolution medium was added to a 2 mL glass vial with a screw cap using a pipette (Eppendorf Research Company). 20 μL of stock solution of each assay compound and QC sample were added to a buffer solution which was equivalent to a kinetic assay solution at pH 7.4. The final concentrations of the assay compound and DMSO solution were 200 μM and 2%, respectively. The vias were capped. The theoretical maximum concentration was 200 μM. The mixture was shaken at 880 rpm at room temperature for 24 hours. The vials were centrifuged at 13,000 rpm for 30 minutes. 200 μL of supernatant was added to a 96-well plate using a digital pipette. The solubility of the assay compound was determined by HPLC spectroscopy, and the results were shown in Table 8.

TABLE 8

Results of kinetic solubility assay

| Compound | Solubility (μM) pH 6.5 |
|---|---|
| 4 | 1.1 |
| Reference example 1 (compound 005-1) | 2.7 |

Conclusion: The solubility of compound 4 of the present disclosure is superior to that of reference example 1.

Assay Example 4: Plasma Protein Binding (PPB) Assay

Assay procedure: 995 μL of blank plasma of various genera were weighed, and 5 μL of assay compound working solution (400 μM) or warfarin working solution (400 μM) was added so that the final concentrations of the assay compound and warfarin in plasma sample were each 2 μM. The samples were mixed thoroughly. The final concentration of DMSO (the organic phase) was 0.5%. 50 μL of the plasma samples of the assay compound and warfarin were pipetted to a sample receiving plate (in triplicate), and the corresponding volume of corresponding blank plasma or buffer was added immediately, so that the final volume in each sample well was 100 μL, wherein the volume ratio of plasma:dialysis buffer was 1:1. 500 μL of stop solution was then added to these samples. These samples were used as $T_0$ samples for determination of recovery and stability. The $T_0$ samples were stored at 2-8° C., waiting for subsequent processing together with other dialyzed samples. 150 μL of the plasma samples of the assay compound and warfarin were added to the dosing side of each dialysis well, and 150 μL of blank dialysis buffer was added to the corresponding receiving side of the dialysis well. The dialysis plate was then placed in a wet 5% $CO_2$ incubator, and incubated with shaking at about 100 rpm at 37° C. for 4 hr. After the dialysis was over, 50 μL of dialyzed buffer sample and dialyzed plasma sample were pipetted to a new sample receiving plate. The corresponding volume of the corresponding blank plasma or buffer solution was added to the samples, so that the final volume in each sample well was 100 μL, wherein the volume ratio of plasma:dialysis buffer was 1:1. All samples were subjected to protein precipitation, and then analyzed by LC/MS/MS. Bound rate and recovery rate of protein were calculated using the following formulae: % Unbound=100*F/T, % Bound=100−% Unbound, % Recovery=100*(F+T)/$T_0$ (wherein F is the peak area ratio of the compound in the dialysate after 4 h of dialysis; T is the peak area ratio of the compound in the plasma after 4 h of dialysis; To is the peak area ratio of the compound in the plasma sample at time zero). The assay results were shown in Table 9:

TABLE 9

Results of PPB assay

| Compound No. | Unbound PPB H/D/C/R/M |
|---|---|
| 4 | 0.4%/0.1%/0.1%/0.2%/0.4% |
| Reference example 1 (compound 005-1) | 0.3%/NA/NA/NA/0.2% |

Conclusion: The binding of compound 4 of the present disclosure to plasma protein is weaker than that of reference example 1.

Assay Example 5: In Vivo Plasma Protein Binding (PPB) Assay in Rat

1. Assay Process 1.1 Preparation of Dialysis Membrane and Matrix

On the day of the assay, frozen plasma was thawed in running cold tap water. After the plasma was completely thawed, the plasma was centrifuged at 3220×g for 5 min, and suspensions and sediments in the plasma were removed.

A double-layer dialysis membrane was soaked in ultrapure water for about 1 h, and then taken out. The double-layer dialysis membrane was divided into two parts, and then soaked in ethanol-water (20:80, v:v) solution for 20 min or placed at 2-8° C. with a validity period of 1 month. Before the start of the assay, the dialysis membrane was rinsed twice with ultrapure water and soaked in ultrapure water for another 20 min for use.

1.2 The Mixing Steps of Compound Sample and the Dilution Process of Control Compound 1.2.1 The Mixing Steps of Compound Sample An appropriate amount of original samples were transferred to a collection tube of mixed samples, and the samples in the collection tube of mixed samples were mixed thoroughly.

1.2.2 The Dilution Process of the Control Compound

The control compound was dissolved in dimethyl sulfoxide to obtain a 10 mM stock solution. A working solution of 400 μM was obtained by dilution with dimethyl sulfoxide. Preparation process of plasma sample: 995 μL of blank plasma was weighed, and 5 μL of warfarin working solution was added. The mixture was mixed thoroughly to obtain a plasma sample with a concentration of 2 μM. The concentration of DMSO (the organic phase) was 0.5%.

1.3 Assay Steps

Preparation process of $T_0$ sample: 30 μL of warfarin plasma samples were pipetted to sample receiving plates (n=3), and 30 μL of blank buffer was added immediately, so that the final volume in each sample well was 60 μL, wherein the volume ratio of plasma:dialysis buffer was 1:1. 300 μL of stop solution was then added to $T_0$ samples of the compound to be assayed and warfarin. The mixtures were stored at 2-8° C., waiting for subsequent processing together with other dialyzed samples.

Dialysis process of plasma sample: 50 μL of plasma sample containing the compound (from the mixed sample tube) and 50 μL of plasma sample containing the control compound were added to the dosing side of each dialysis well (n=3), and 50 μL of blank dialysis buffer was added to the corresponding receiving side of the dialysis well. The dialysis plate was placed in a 5% $CO_2$ incubator, and incubated with shaking at 100 rpm at 37° C. for 4 h.

After the dialysis was over, 30 μL of dialyzed buffer sample (dialysate) and dialyzed plasma sample were pipetted to a new 96-well plate (a sample receiving plate). The corresponding volume of the corresponding blank plasma or buffer solution was added to the samples, so that the final volume in each sample well was 60 μL, wherein the volume ratio of plasma:dialysis buffer was 1:1. 300 μL of stop solution was added to all samples and all mixtures were shaken thoroughly. After being shaken, the samples were centrifuged at 4000 rpm for 20 minutes. After protein precipitation, 100 μL of supernatant was taken for LC-MS/MS analysis, and the results were shown in Table 10.

TABLE 10

Results of PPB assay

| Compound No. | Unbound PPB |
|---|---|
| 4 | 0.2% [a] |
| Reference example 1 (compound 005-1) | 0.1% [b] |

Note:
[a] average of 3 results,
[b] average of 4 results.
Conclusion: The binding of compound 4 of the present disclosure to rat plasma protein is weaker than that of reference example 1.

Assay Example 6: Pharmacokinetic Evaluation of Compound in Mouse

Assay purpose: To assay the pharmacokinetics of the compound in CD-1 mouse (intravenous)

Pharmacokinetic study of oral and intravenously injected compound 4 and reference example 1 (compound 005-1) in CD-1 mouse Compound 4 and reference example 1 were mixed with the solvent (10% NMP/60% PEG400/30% $H_2O$). The mixture was vortexed and sonicated to prepare a clarified solution of 0.1 mg/mL. 7- to 10-week old CD-1 male mice were selected, and the candidate compound solution was administered intravenously at a dose of 0.21 mg/kg.

Whole blood was collected for a certain period of time to prepare the plasma. Drug concentration was analyzed by LC-MS/MS, and pharmacokinetic parameters were calculated by Phoenix WinNonlin software (Pharsight, USA). The results were shown in Table 11.

TABLE 11

Intravenous (IV) PK data

| Assay sample (compound prepared in each example) | Reference example 1 (compound 005-1) | 4 |
|---|---|---|
| Dosage (mg/kg) | 021 | 0.21 |
| $C_0$ (nM) | 1038 | 562 |
| $T_{1/2}$ (h) | 4.34 | 4.65 |
| Vd (L/kg) | 0.70 | 0.85 |
| Cl (mL/Kg/min) | 2.01 | 2.12 |
| $AUC_{0-inf}$ (nM · h) | 3493 | 3107 |
| $AUC_u$ (nM · h) | 7.0 | 12.4 |

Note:
$AUC_u = AUC_{0-inf} *$ Unbound PPB (Mouse)
Conclusion: The free drug concentration of compound 4 of the present disclosure in mouse plasma is higher than that of reference example 1.

Assay Example 6-1: Pharmacokinetic Evaluation of Compound in Mouse

Assay purpose: To assay the pharmacokinetics of the compound in CD-1 mouse (oral)

Pharmacokinetic study of oral and intravenously injected compound 4 and reference example 1 (compound 005-1) in CD-1 mouse.

Compound 4 and reference example 1 (compound 005-1) were mixed with the solvent (10% NMP/60% PEG400/30% $H_2O$). The mixture was vortexed and sonicated to prepare a clarified solution of 0.6 mg/mL. 7- to 10-week old CD-1 male mice were selected, and the candidate compound solution was administered orally by gavage at a dose of 3.1 mg/kg.

Whole blood was collected for a certain period of time to prepare the plasma. Drug concentration was analyzed by LC-MS/MS, and pharmacokinetic parameters were calculated by Phoenix WinNonlin software (Pharsight, USA). The results were shown in Table 12.

TABLE 12

Oral (PO) PK data

| Assay sample | Reference example 1 (compound 005-1) | 4 |
|---|---|---|
| Dosage (mg/kg) | 3.1 | 3.1 |
| $C_{max}$ (nM) | 3835 | 2975 |
| Tmax | 8.0 | 6 |
| $T_{1/2}$ (h) | 3.75 | 3.73 |
| $AUC_{0-inf}$ (nM · h) | 44124 | 33246 |
| $AUC_u$ (nM · h) | 88.2 | 133.0 |
| F % | 83.8 | 71.7 |

Note:
$AUC_u = AUC_{0-inf} *$ Unbound PPB (Mouse)
Conclusion: The free drug concentration of compound 4 of the present disclosure in mouse plasma is higher than that of reference example 1.

Assay Example 7: Pharmacokinetic Evaluation of Compound in Rat

Assay purpose: To assay the pharmacokinetics of the compound in SD rat (intravenous)

Pharmacokinetic study of oral and intravenously injected compound 4 and reference example 1 in SD rat.

Compound 4 and reference example 1 were mixed with the solvent (10% NMP/60% PEG400/30% H$_2$O). The mixture was vortexed and sonicated to prepare a clarified solution of 0.5 mg/mL. 7- to 10-week old SD rats were selected, and the candidate compound solution was administered intravenously at a dose of 0.5 mg/kg. Whole blood was collected for a certain period of time to prepare the plasma. Drug concentration was analyzed by LC-MS/MS, and pharmacokinetic parameters were calculated by Phoenix WinNonlin software (Pharsight, USA). The results were shown in Table 13.

TABLE 13

Intravenous (IV) PK data

| Assay sample | Reference example 1 (compound 005-1) | 4 |
|---|---|---|
| Dosage (mg/kg) | 0.51 | 0.49 |
| $C_0$ (nM) | 800 | 852 |
| $T_{1/2}$ (h) | 2.02 | 1.82 |
| Vd (L/kg) | 1.57 | 1.42 |
| Cl (mL/Kg/min) | 9.08 | 9.80 |
| $AUC_{0\text{-}inf}$ (nM · h) | 1922 | 1695 |
| $AUC_u$ (nM · h) | 1.9 | 3.4 |

Note:
$AUC_u = AUC_{0\text{-}inf}$ * Unbound PPB (in vivo assay of PPB in rat)
Conclusion: The free drug concentration of compound 4 of the present disclosure in rat plasma is higher than that of reference example 1.

Assay Example 7-1: Pharmacokinetic Evaluation of Compound in SD Rat

Assay purpose: To assay the pharmacokinetics of the compound in SD rat (oral)

Pharmacokinetic study of oral and intravenously injected compound 4 and reference example 1 in SD rat.

Compound 4 and reference example 1 were mixed with the solvent (10% NMP/60% PEG400/30% H$_2$O). The mixture was vortexed and sonicated to prepare a clarified solution of 2 mg/mL. 7- to 10-week old SD rats were selected, and the candidate compound solution was administered orally by gavage at a dose of 2 mg/kg.

Whole blood was collected for a certain period of time to prepare the plasma. Drug concentration was analyzed by LC-MS/MS, and pharmacokinetic parameters were calculated by Phoenix WinNonlin software (Pharsight, USA). The results were shown in Table 14.

TABLE 14

Oral (PO) PK data

| Assay sample | Reference example 1 (compound 005-1) | 4 |
|---|---|---|
| Dosage (mg/kg) | 1.9 | 1.8 |
| $C_{max}$ (nM) | 607 | 587 |
| Tmax | 2.00 | 2.00 |
| $T_{1/2}$ (h) | 2.41 | 2.33 |
| $AUC_{0\text{-}inf}$ (nM · h) | 5033 | 3887 |
| $AUC_u$ (nM · h) | 5.0 | 7.8 |
| F % | 65.5 | 57.3 |

Note:
$AUC_u = AUC_{0\text{-}inf}$ * Unbound PPB (in vivo assay of PPB in rat)
Conclusion: The free drug concentration of compound 4 of the present disclosure in rat plasma is higher than that of reference example 1.

Assay Example 8: In Vivo Study

Xenograft tumor model of TMD8 in SCID mouse:

Assay method: A tumor model of subcutaneously transplanted human diffuse large B lymphoma in mice was established. Tumor cells in logarithmic growth phase were collected, counted, and then resuspended in RPMI1640. The cell suspension was adjusted to a concentration of $4 \times 10^7$/mL, and mixed well with Matrigel (1:1). Tumor cells were inoculated subcutaneously on the right back of the mouse with a 1 mL syringe (4-gauge needle), $4 \times 10^6$ cells/mouse. When the animal tumor reached about 100-300 mm$^3$, the tumor-bearing mice were randomly divided into 6 groups according to the size of the tumor volume, with 6 mice in each group. On the day of the assay, the animals were administered the corresponding drugs according to the corresponding groups. The first group G1 was set as a negative control group, which was administered 10% NMP/60% PEG400/30% H$_2$O by gavage alone. The second group G2 was set as a positive control group, which was given reference example 1 (compound 005-1) at a dose of 30 mg/kg. The third group G3 was given compound 4 at a dose of 30 mg/kg, once a day, for a total of 15 days.

TABLE 15

Pharmacodynamic study of the assay compound on the transplanted tumor of human diffuse large B lymphoma TMD8 in mouse

| Group | Number of animals | Assay compound | Dosage (mg/kg) | Dosing concentration (mg/mL) | Dosing volume (mL/kg) | Route and frequency of dosing |
|---|---|---|---|---|---|---|
| G1 | 6 | Negative control | (N/A) | (N/A) | (N/A) | PO, QD*15 |
| G2 | 6 | Reference example 1 | 30 | 10 | 3 | PO, QD*15 |
| G3 | 6 | Compound 4 | 30 | 10 | 3 | PO, QD*15 |

Note:
PO means oral, and QD means once a day.

During the assay, animal weight and tumor size were measured 3 times a week, and clinical symptoms of animals were observed and recorded every day. Each dosing was referenced to the most recent animal weight.

For tumor measurement, length (a) and width (b) were measured with digital vernier calipers, and the calculation formula for tumor volume (TV) was: TV=a×b²/2.

Assay Results:

Effect of Each Assay Compound on Tumor Volume of Human Diffuse Large B Lymphoma TMD8 in Mouse Reference example 1 and compound 4 both have a certain inhibitory effect on xenograft tumor of human diffuse large B lymphoma TMD8 in mouse:

The inhibitory effect of reference example 1 on xenograft tumor of human diffuse large B lymphoma in mouse was significantly different on the 10th day, and the relative tumor proliferation rate T/C was 48.05% (P<0.01, two-tailed t-test). On the 14th day, the relative tumor proliferation rate was 37.28% (P<0.001, two-tailed t-test), and the tumor volume inhibition rate TGI (%) was 61.70%.

Figure 5:
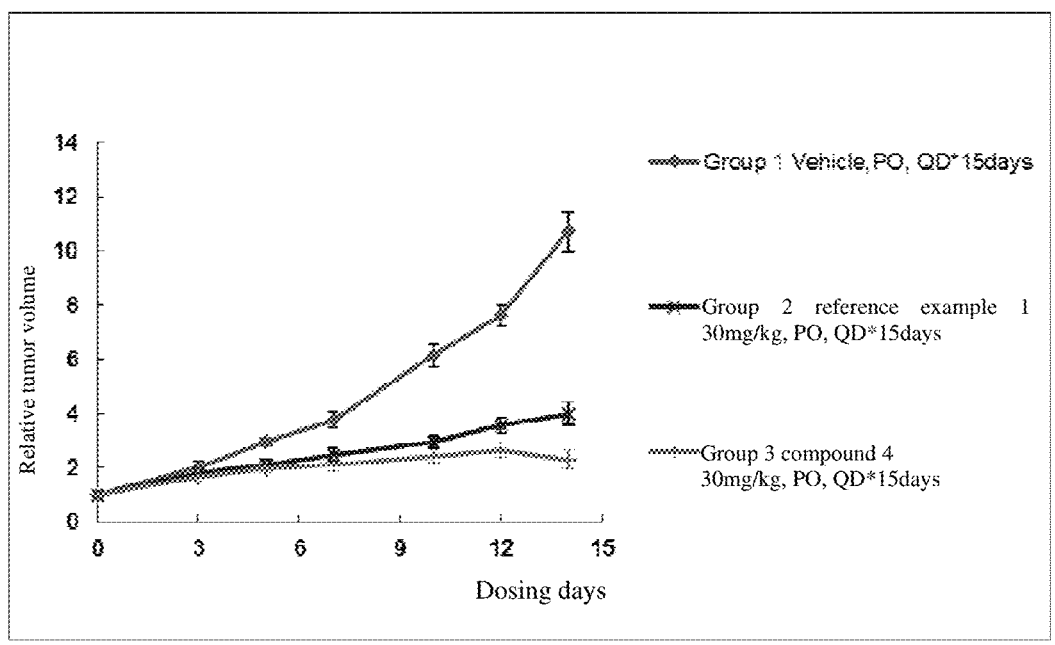
FIG. 5: effect of the assay compound on tumor volume of xenograft tumor of human diffuse large B lymphoma TMD8 in mouse (Day 14) (Mean SEM).

The inhibitory effect of compound 4 on xenograft tumor of human diffuse large B lymphoma in mouse was significantly different on the 5th day, and the relative tumor proliferation rate T/C was 66.33% (P<0.05, two-tailed t-test). On the 14th day, the relative tumor proliferation rate was 21.53% (P<0.001, two-tailed t-test), and the tumor volume inhibition rate TGI (%) was 79.04%. Detailed results were shown in FIG. 5 and Table 16 of the specification.

TABLE 16

Effect of the assay compound on animal tumor size in xenograft tumor model of human diffuse large B lymphoma TMD8 in mouse

| Group | Number of animals | Assay compound | Dosing frequency | Dosage mg/kg | Relative tumor proliferation rate T/C (%) | Tumor volume inhibition rate TGI (%) |
|---|---|---|---|---|---|---|
| 1 | 6 | Negative control | QD × 15 | NA | N/A | N/A |
| 2 | 6 | Reference example 1 | QD × 15 | 30 | 37.28% | 61.70% |
| 3 | 6 | Compound 4 | QD × 15 | 30 | 21.53% | 79.04% |

Note:
N/A means not detected.
Assay conclusion: In the aspect of in vivo efficacy, the compound 4 of the present disclosure has significantly better inhibitory effect on tumor than the reference example 1.

What is claimed is:

1. A compound represented by formula (III) or a pharmaceutically acceptable salt thereof,

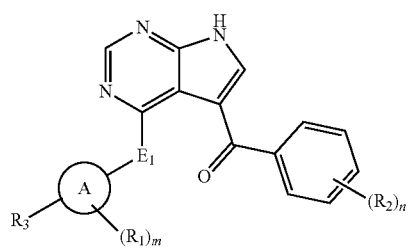

wherein, $R_1$ is $C_{1-3}$ alkoxy, wherein the $C_{1-3}$ alkoxy is optionally substituted by 1, 2, or 3 $R_a$;

each $R_a$ is selected from the group consisting of D, halogen, and OH;

$R_2$ is selected from the group consisting of halogen, methyl, phenoxy, and pyridyloxy, wherein the phenoxy and pyridyloxy are optionally substituted with 1, 2 or 3 halogens;

$R_3$ is -CH$_2$OH m is 1 or 2;

n is 1, 2, or 3;

$E_1$ is selected from the group consisting of O, S and NH; and ring A is

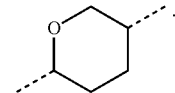

2. The compound or pharmaceutically acceptable salt thereof according to claim 1, wherein each Ra is selected from the group consisting of D, F, and OH.

3. The compound or pharmaceutically acceptable salt thereof according to claim 1, wherein R1 is selected from the group consisting of OCH$_3$, OCD$_3$, and OCH$_2$CH$_2$OH.

4. The compound or pharmaceutically acceptable salt thereof according to claim 1, wherein $R_2$ is selected from the group consisting of F, Cl, methyl, phenoxy, 2-fluorophenoxy, and 2-pyridyloxy.

5. The compound or pharmaceutically acceptable salt thereof according to claim 1, wherein $E_1$ is NH.

6. The compound or pharmaceutically acceptable salt thereof according to claim 1, which is

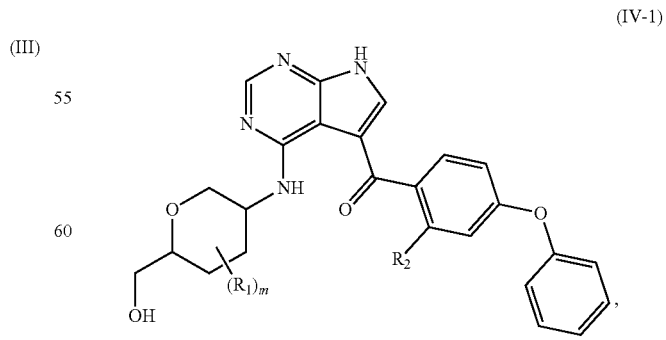

wherein $R_1$, $R_2$ and m are as defined in claim 1.

7. A compound represented by the following formula or a pharmaceutically acceptable salt thereof, which is selected from the group consisting of:
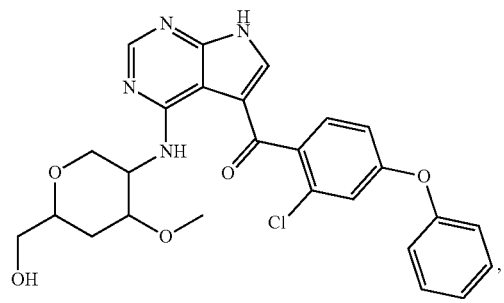
,
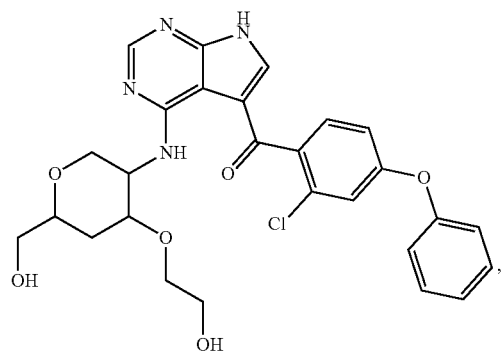
,
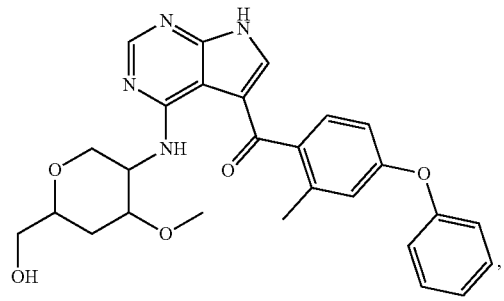
,
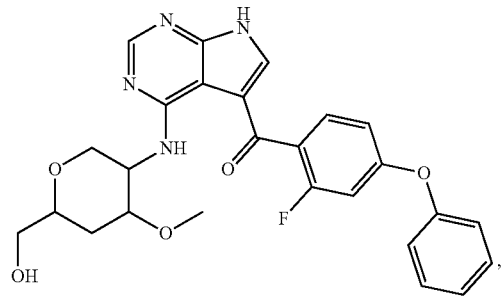
,
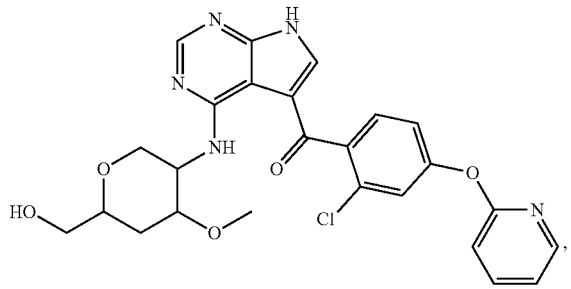
,
-continued
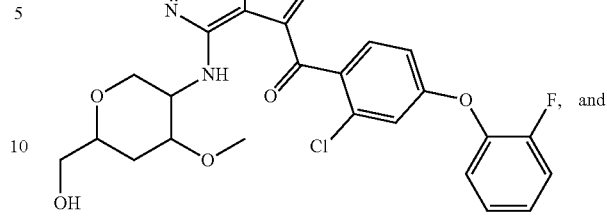
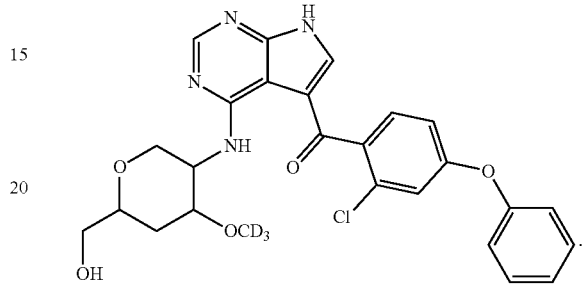
, and
8. The compound or pharmaceutically acceptable salt thereof according to claim 7, which is selected from the group consisting of:
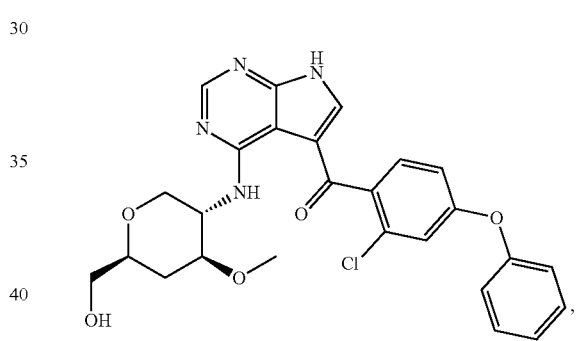
,
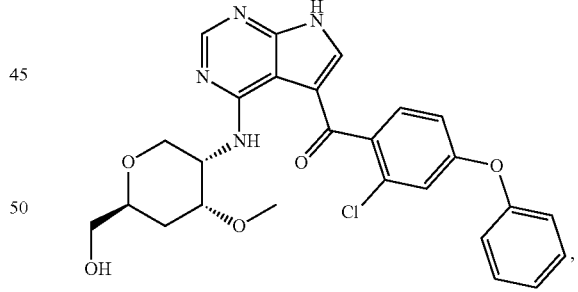
,
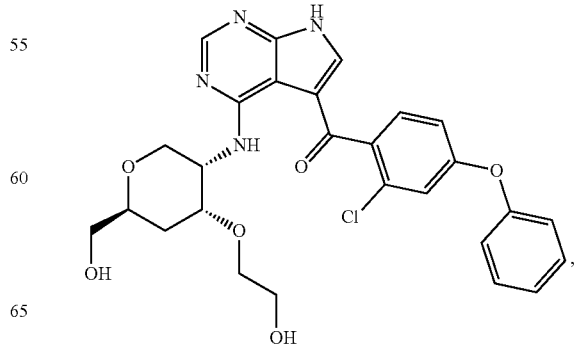
,

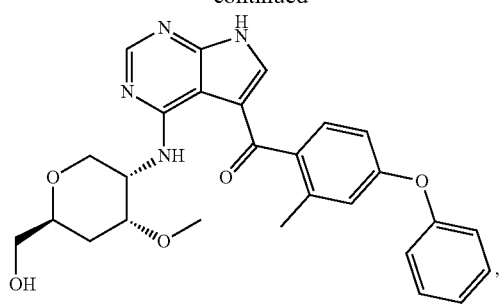

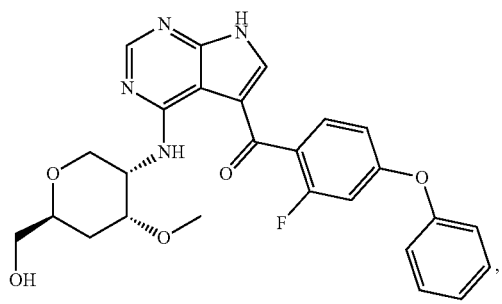

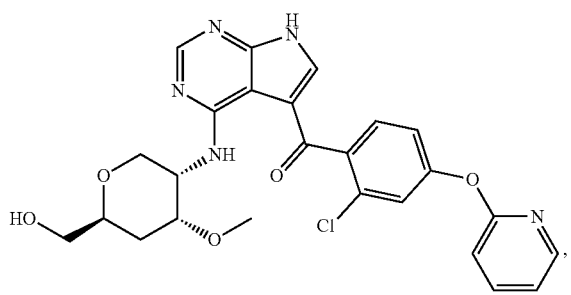

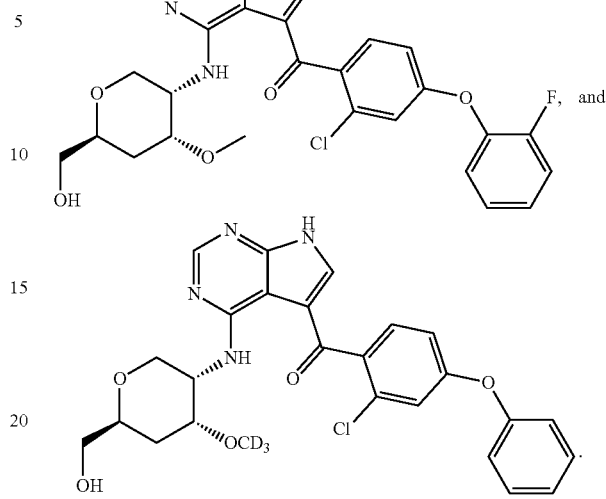

9. A method of treating a lymphoma in a subject in need thereof, comprising administering to the subject the compound or pharmaceutically acceptable salt thereof according to claim 1.

10. A method of treating a lymphoma in a subject in need thereof, comprising administering to the subject the compound or pharmaceutically acceptable salt thereof according to claim 7.

11. A method of treating a lymphoma in a subject in need thereof, comprising administering to the subject the compound or pharmaceutically acceptable salt thereof according to claim 8.

* * * * *